US012588990B2

(12) United States Patent
Cohen et al.

(10) Patent No.: US 12,588,990 B2
(45) Date of Patent: Mar. 31, 2026

(54) DELIVERY APPARATUS FOR A PROSTHETIC HEART VALVE

(71) Applicant: EDWARDS LIFESCIENCES CORPORATION, Irvine, CA (US)

(72) Inventors: Oren Cohen, Kadima (IL); Ofir Witzman, Harish (IL)

(73) Assignee: Edwards Lifesciences Corporation, Irvine, CA (US)

( * ) Notice: Subject to any disclaimer, the term of this patent is extended or adjusted under 35 U.S.C. 154(b) by 189 days.

(21) Appl. No.: 18/528,619

(22) Filed: Dec. 4, 2023

(65) Prior Publication Data

US 2024/0099837 A1     Mar. 28, 2024

Related U.S. Application Data

(63) Continuation of application No. 17/228,184, filed on Apr. 12, 2021, now Pat. No. 11,890,189, which is a continuation of application No. 15/959,623, filed on Apr. 23, 2018, now Pat. No. 10,973,634.

(60) Provisional application No. 62/490,210, filed on Apr. 26, 2017.

(51) Int. Cl.
| | |
|---|---|
| *A61F 2/24* | (2006.01) |
| *A61F 2/844* | (2013.01) |
| *A61F 2/95* | (2013.01) |

(52) U.S. Cl.
CPC .......... *A61F 2/2427* (2013.01); *A61F 2/2418* (2013.01); *A61F 2/2439* (2013.01); *A61F 2/2436* (2013.01); *A61F 2/844* (2013.01); *A61F 2/9517* (2020.05); *A61F 2220/0091* (2013.01)

(58) Field of Classification Search
CPC ........ A61F 2/24; A61F 2/2427; A61F 2/9517; A61F 2002/9534; A61F 2220/0091
See application file for complete search history.

(56) References Cited

U.S. PATENT DOCUMENTS

| | | |
|---|---|---|
| 519,297 A | 5/1894 | Wanek et al. |
| 4,035,849 A | 7/1977 | Angell et al. |
| 4,592,340 A | 6/1986 | Boyles |
| 4,955,895 A | 9/1990 | Sugiyama et al. |
| 4,994,077 A | 2/1991 | Dobben |
| 5,059,177 A | 10/1991 | Towne et al. |
| 5,176,698 A | 1/1993 | Burns et al. |
| 5,192,297 A | 3/1993 | Hull |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Martin T Ton
(74) *Attorney, Agent, or Firm* — Klarquist Sparkman, LLP

(57)     ABSTRACT

In one embodiment, a delivery apparatus handle, such as for a mechanical heart valve frame can comprise an actuation knob with a toggle mechanism that can toggle the actuation knob from a first state in which the actuation knob is operable to cause the linear or rotational movement of multiple elements or sets of elements, such as tubes that are attached to, e.g., a mechanical heart valve frame to cause expansion or collapsing of the frame, to a second state in which only a single element or set of elements is moved, allowing for additional operations, such as, e.g., locking the frame and/or releasing it from the delivery apparatus.

18 Claims, 18 Drawing Sheets

(56)  References Cited

U.S. PATENT DOCUMENTS

| | | | |
|---|---|---|---|
| 5,266,073 A | 11/1993 | Wall | |
| 5,325,845 A | 7/1994 | Adair | |
| 5,358,496 A | 10/1994 | Ortiz et al. | |
| 5,411,552 A | 5/1995 | Andersen et al. | |
| 5,554,185 A | 9/1996 | Block et al. | |
| 5,591,195 A | 1/1997 | Taheri et al. | |
| 5,599,305 A | 2/1997 | Hermann et al. | |
| 5,632,760 A | 5/1997 | Sheiban et al. | |
| 5,639,274 A | 6/1997 | Fischell et al. | |
| 5,728,068 A | 3/1998 | Leone et al. | |
| 5,749,890 A | 5/1998 | Shaknovich | |
| 5,782,809 A | 7/1998 | Umeno et al. | |
| 5,824,044 A | 10/1998 | Quiachon et al. | |
| 5,840,081 A | 11/1998 | Andersen et al. | |
| 5,908,405 A | 6/1999 | Imran et al. | |
| 5,916,147 A | 6/1999 | Boury | |
| 5,944,690 A | 8/1999 | Falwell et al. | |
| 5,961,536 A | 10/1999 | Mickley et al. | |
| 5,968,068 A | 10/1999 | Dehdashtian et al. | |
| 6,019,777 A | 2/2000 | Mackenzie | |
| 6,027,510 A | 2/2000 | Alt | |
| 6,033,381 A | 3/2000 | Kontos | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,379,372 B1 | 4/2002 | Dehdashtian et al. | |
| 6,383,171 B1 | 5/2002 | Gifford et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,471,672 B1 | 10/2002 | Brown et al. | |
| 6,500,147 B2 | 12/2002 | Omaleki et al. | |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,137,993 B2 | 11/2006 | Acosta et al. | |
| 7,276,084 B2 | 10/2007 | Yang et al. | |
| 7,318,278 B2 | 1/2008 | Zhang et al. | |
| 7,320,702 B2 | 1/2008 | Hammersmark et al. | |
| 7,320,704 B2 | 1/2008 | Lashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,510,575 B2 | 3/2009 | Spenser et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,780,723 B2 | 8/2010 | Taylor | |
| 7,785,366 B2 | 8/2010 | Maurer et al. | |
| 7,959,661 B2 | 6/2011 | Hijlkema et al. | |
| 8,029,556 B2 | 10/2011 | Rowe | |
| 8,167,932 B2 | 5/2012 | Bourang et al. | |
| RE43,882 E | 12/2012 | Hopkins et al. | |
| 8,449,606 B2 | 5/2013 | Eliasen et al. | |
| 8,475,523 B2 | 7/2013 | Duffy | |
| 8,568,472 B2 | 10/2013 | Marchand et al. | |
| 9,061,119 B2 | 6/2015 | Le et al. | |
| 9,119,716 B2 | 9/2015 | Lee et al. | |
| 9,795,477 B2 | 10/2017 | Tran et al. | |
| 11,273,038 B2 | 3/2022 | Tang et al. | |
| 2001/0002445 A1 | 5/2001 | Vesely | |
| 2001/0007082 A1 | 7/2001 | Dusbabek et al. | |
| 2002/0032481 A1 | 3/2002 | Gabbay | |
| 2002/0058995 A1 | 5/2002 | Stevens | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0120341 A1 | 6/2003 | Shennib et al. | |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0080474 A1 | 4/2005 | Andreas et al. | |
| 2005/0096736 A1 | 5/2005 | Osse et al. | |
| 2005/0137689 A1 | 6/2005 | Salahieh et al. | |
| 2005/0149159 A1* | 7/2005 | Andreas | A61M 25/0136 |
| | | | 623/1.11 |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2005/0245894 A1 | 11/2005 | Zadno Azizi | |
| 2006/0025857 A1 | 2/2006 | Bergheim et al. | |
| 2006/0282150 A1* | 12/2006 | Olson | A61M 25/0136 |
| | | | 623/1.11 |
| 2007/0005131 A1 | 1/2007 | Taylor | |
| 2007/0073389 A1 | 3/2007 | Bolduc et al. | |
| 2007/0088431 A1 | 4/2007 | Bourang et al. | |
| 2007/0100356 A1 | 5/2007 | Lucatero et al. | |
| 2007/0112422 A1 | 5/2007 | Dehdashtian | |
| 2007/0203503 A1* | 8/2007 | Salahieh | A61F 2/2436 |
| | | | 623/2.11 |
| 2007/0203575 A1 | 8/2007 | Forster et al. | |
| 2007/0219612 A1 | 9/2007 | Andreas et al. | |
| 2007/0239254 A1 | 10/2007 | Chia et al. | |
| 2007/0244546 A1 | 10/2007 | Francis | |
| 2007/0265700 A1 | 11/2007 | Eliasen et al. | |
| 2008/0065011 A1 | 3/2008 | Marchand et al. | |
| 2008/0103520 A1 | 5/2008 | Selkee | |
| 2008/0125853 A1 | 5/2008 | Bailey et al. | |
| 2008/0294230 A1 | 11/2008 | Parker | |
| 2009/0024428 A1 | 1/2009 | Hudock | |
| 2009/0069889 A1 | 3/2009 | Suri et al. | |
| 2009/0138079 A1 | 5/2009 | Tuval et al. | |
| 2009/0157175 A1 | 6/2009 | Benichou | |
| 2009/0192585 A1 | 7/2009 | Bloom et al. | |
| 2009/0228093 A1 | 9/2009 | Taylor et al. | |
| 2009/0276040 A1 | 11/2009 | Rowe et al. | |
| 2009/0281619 A1 | 11/2009 | Le et al. | |
| 2009/0299456 A1 | 12/2009 | Melsheimer | |
| 2009/0319037 A1 | 12/2009 | Rowe et al. | |
| 2010/0030318 A1 | 2/2010 | Berra | |
| 2010/0036472 A1 | 2/2010 | Papp | |
| 2010/0036473 A1 | 2/2010 | Roth | |
| 2010/0049313 A1 | 2/2010 | Alon et al. | |
| 2010/0076402 A1 | 3/2010 | Mazzone et al. | |
| 2010/0076541 A1 | 3/2010 | Kumoyama | |
| 2010/0082089 A1 | 4/2010 | Quadri et al. | |
| 2010/0094394 A1 | 4/2010 | Beach et al. | |
| 2010/0121425 A1 | 5/2010 | Shimada | |
| 2010/0145431 A1 | 6/2010 | Wu et al. | |
| 2010/0161036 A1 | 6/2010 | Pintor et al. | |
| 2010/0174363 A1 | 7/2010 | Castro | |
| 2010/0198347 A1 | 8/2010 | Zakay et al. | |
| 2010/0274344 A1 | 10/2010 | Dusbabek et al. | |
| 2010/0280605 A1* | 11/2010 | Hammer | A61F 2/2436 |
| | | | 623/2.11 |
| 2011/0015729 A1 | 1/2011 | Jimenez et al. | |
| 2011/0054596 A1 | 3/2011 | Taylor | |
| 2011/0137331 A1 | 6/2011 | Walsh et al. | |
| 2011/0160846 A1 | 6/2011 | Bishop et al. | |
| 2012/0123529 A1 | 5/2012 | Levi et al. | |
| 2012/0239142 A1 | 9/2012 | Liu et al. | |
| 2013/0030519 A1 | 1/2013 | Tran et al. | |
| 2013/0317598 A1 | 11/2013 | Rowe et al. | |
| 2014/0296962 A1 | 10/2014 | Cartledge et al. | |

(56)            References Cited

U.S. PATENT DOCUMENTS

| | | |
|---|---|---|
| 2017/0065415 A1 | 3/2017 | Rupp et al. |
| 2018/0153689 A1 | 6/2018 | Maimon et al. |
| 2018/0344456 A1 | 12/2018 | Barash et al. |

FOREIGN PATENT DOCUMENTS

| | | | |
|---|---|---|---|
| EP | 0592410 | B1 | 10/1995 |
| EP | 0850607 | A1 | 7/1998 |
| FR | 2815844 | A1 | 5/2002 |
| WO | 1991017720 | A1 | 11/1991 |
| WO | 1998029057 | A1 | 7/1998 |
| WO | 1999012483 | A1 | 3/1999 |
| WO | 2001049213 | A2 | 7/2001 |
| WO | 2001054625 | A1 | 8/2001 |
| WO | 2001076510 | A2 | 10/2001 |
| WO | 2002022054 | A1 | 3/2002 |
| WO | 2002036048 | A1 | 5/2002 |
| WO | 2002047575 | A2 | 6/2002 |
| WO | 2002060352 | A1 | 8/2002 |
| WO | 2003030776 | A2 | 4/2003 |
| WO | 2003047468 | A1 | 6/2003 |
| WO | 2004019825 | A1 | 3/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2010121076 | A2 | 10/2010 |

* cited by examiner

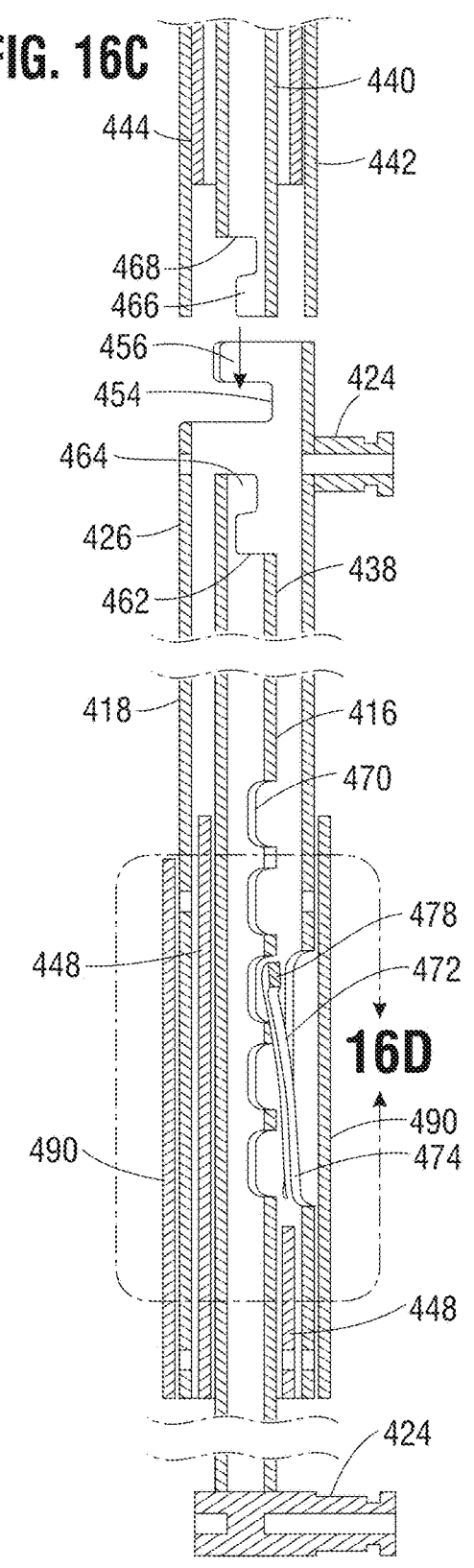
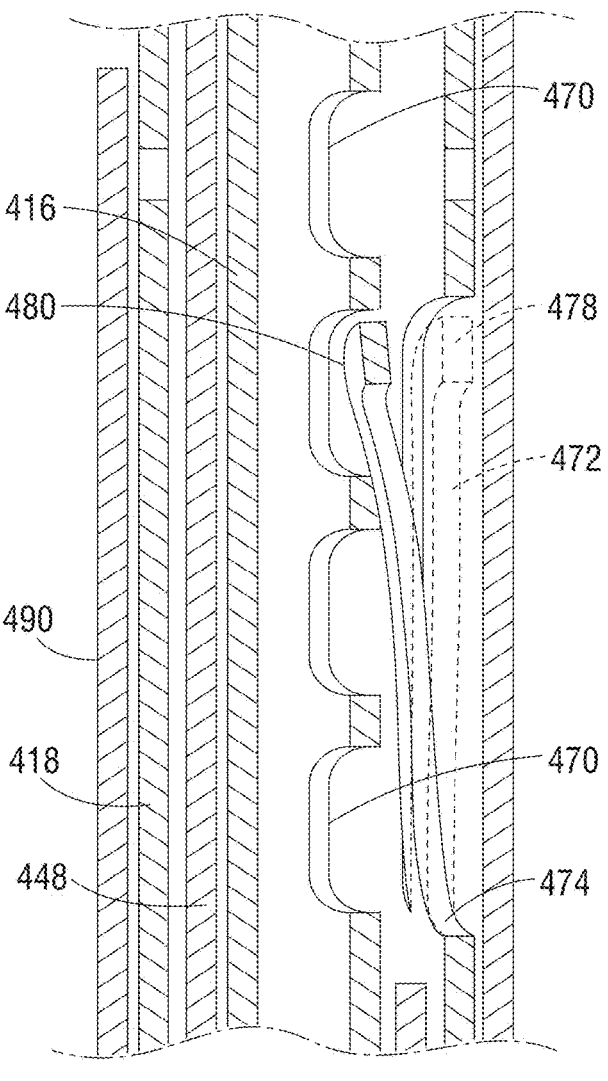

FIG. 19

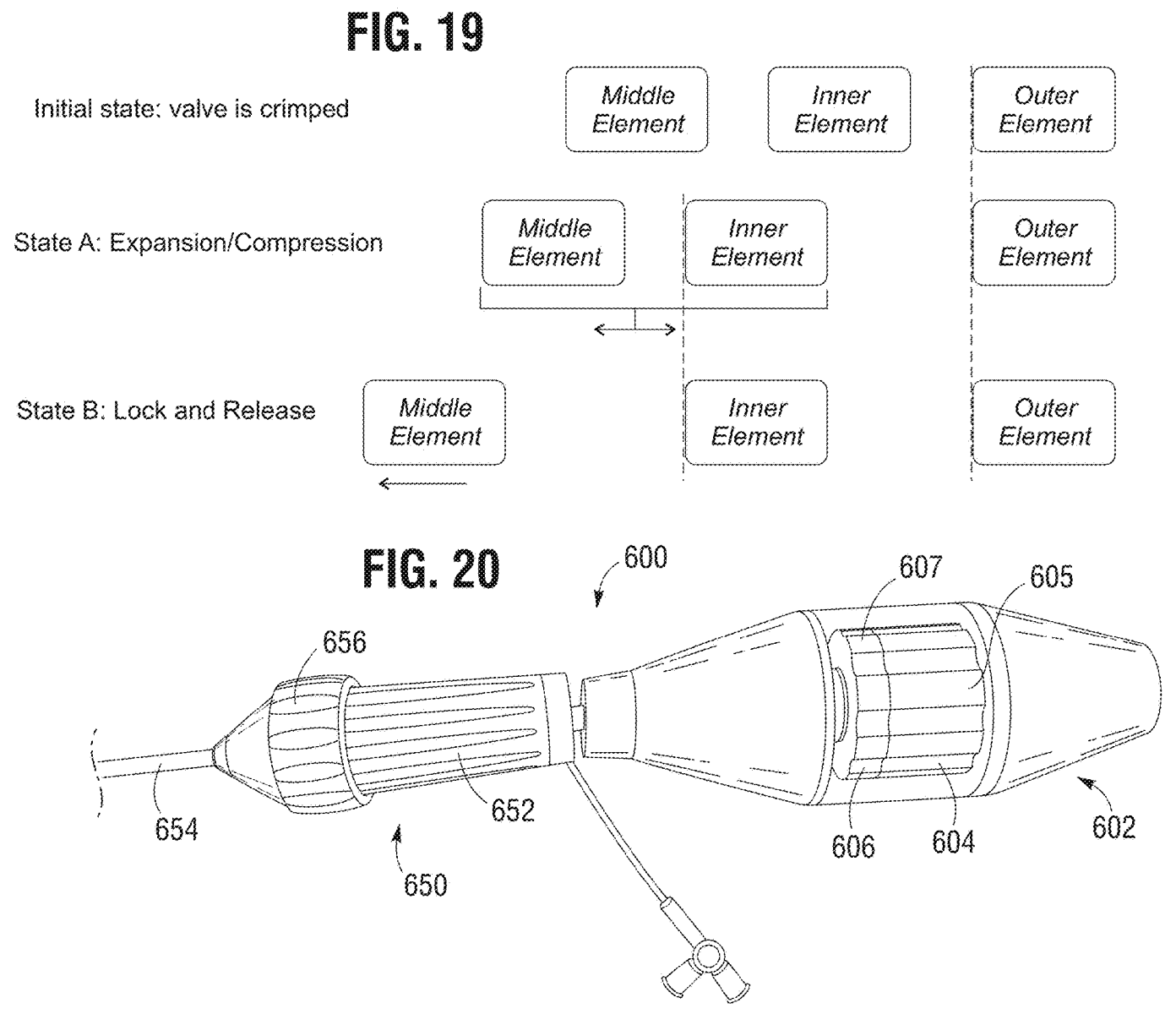

Initial state: valve is crimped

| Middle Element | Inner Element | Outer Element |

State A: Expansion/Compression

| Middle Element | Inner Element | Outer Element |

| | Inner Element | Outer Element |

State B: Lock and Release

| Middle Element |

DELIVERY APPARATUS FOR A PROSTHETIC HEART VALVE

CROSS REFERENCE TO RELATED APPLICATIONS

This application is a continuation of U.S. patent application Ser. No. 17/228,184, filed Apr. 12, 2021, which is a continuation of U.S. patent application Ser. No. 15/959,623, filed Apr. 23, 2018, now U.S. Pat. No. 10,973,634, which claims the benefit of U.S. Provisional Application Ser. No. 62/490,210, entitled DELIVERY APPARATUS FOR A PROSTHETIC HEART VALVE, filed on Apr. 26, 2017. The prior applications are incorporated herein by reference in their entirety.

FIELD

The present disclosure relates to implantable, mechanically expandable prosthetic devices, such as prosthetic heart valves, and to methods and delivery assemblies for, and including, such prosthetic devices.

BACKGROUND

Malfunctions within the human heart, such as those resulting from valvular diseases, frequently require repair of the native valve or replacement of the native valve with an artificial valve. There are a number of known repair devices (e.g., stents) and artificial valves, as well as a number of known methods of implanting these devices and valves in humans. In one known technique, a prosthetic device is configured to be implanted in a less invasive procedure by way of catheterization. For example, a collapsible transcatheter prosthetic heart valve can be crimped to a compressed state and percutaneously introduced in the compressed state on a catheter and expanded to a functional size at the desired position by mechanical expansion or using a self-expanding frame or stent.

SUMMARY

Embodiments of improved prosthetic implant delivery assemblies and frames therefor are disclosed herein, as well as related methods and devices for such assemblies. In several embodiments, the disclosed assemblies are configured for delivering replacement heart valves into a heart of a patient.

In one representative embodiment, a delivery apparatus comprises a handle, at least a first element, a second element, and a third element extending from the handle, an actuation knob configured to actuate at least one of the elements, a toggle configured to toggle the actuation knob between a first state and a second state, wherein when the actuation knob is in the first state, rotation of the actuation knob moves the first and second elements axially relative to the third element, and wherein when the actuation knob is in the second state, rotation of the actuation knob moves the first element axially relative to the second and third elements.

In one particular embodiment, a toggle is movable relative to an actuation knob from a first toggle position to a second toggle position to toggle the actuation knob from a first state to a second state, and vice versa. In another more particular embodiment, the toggle comprises a toggle knob which can be rotated in a first direction to move from a first toggle position to a second toggle position.

In still another particular embodiment, a rotatable component is disposed in a handle, and an actuation knob is operatively coupled to a first element and the rotatable component is operatively coupled to a second element such that when the actuation knob is in a first state, rotation of the actuation knob causes corresponding rotation of the rotatable component, the rotation of the actuation knob causing axial movement of the first element and the rotation of the rotatable component causing axial movement of the second element. In a more particular embodiment, when the actuation knob is in a second state, rotation of the actuation knob causes axial movement of the first element but does not cause corresponding rotation of the rotatable component and axial movement of the second element.

In another particular embodiment, one or more plungers are disposed between a toggle and an actuation knob, wherein the toggle is configured to move the plungers between a first plunger position and a second plunger position upon movement of the toggle toward and away from the actuation knob. In a still more particular embodiment, when the plungers are in the first plunger position, the plungers extend through the actuation knob and into a rotatable component such that rotation of the actuation knob causes rotation of the rotatable component and when the plungers are in the second position, the plungers are withdrawn from the rotatable component such that rotation of the actuation knob does not cause corresponding rotation of the rotatable component. In another more particular embodiment, the apparatus further comprises one or more springs that are configured to bias the one or more plungers to the second plunger position. In still another more particular embodiment, each of the plungers extends through an aperture in the actuation knob and into an opening in the rotatable component when the plungers are in the first plunger position, and each of the plunger is withdrawn from the corresponding opening in the rotatable component when the plungers are in the second plunger position.

In still another particular embodiment, the apparatus further comprises a first nut threadably engaging a corresponding threaded portion of the actuation knob and coupled to a proximal end portion of the first element; and a second nut threadably engaging a corresponding threaded portion of the rotatable component and coupled to a proximal end portion of the second element, wherein rotation of the actuation knob causes corresponding axial movement of the first nut and the first element and rotation of the rotatable component causes corresponding axial movement of the second nut and the second element. In still another more particular embodiment, the first element extends axially through an aperture in the second nut.

In another particular embodiment, the delivery apparatus is combined with a prosthetic heart valve, wherein: the prosthetic heart valve comprises a radially expandable and compressible frame that is expandable from a radially compressed, delivery state to a radially expanded state; the first, second, and third elements have respective distal end portions releasably coupled to the frame; and rotation of the actuation knob when in the first state is effective to radially expand the frame from the delivery state to the expanded state, and rotation of the actuation knob when in the second state is effective to release the frame from the distal end portions of the first, second, and third elements.

In another particular embodiment, the frame comprises at least one expansion and locking unit comprising first and second members, the first member being configured to apply a proximally directed force to the frame and the second member being configured to apply a distally directed force to the frame such that relative axial movement between first and second members is effective to radially expand or compress the frame. In still another more particular embodiment the first and second members comprise respective, matable locking features configured to retain the frame in the expanded state when the locking feature of the first member engages the locking feature of the second member. In still another more particular embodiment, the distal end portion of the first element extends between the first and second members and prevents the locking feature of the first member from engaging the locking feature of the second member. In still another more particular embodiment the distal end portion of the second element is releasably connected to the first member and the distal end portion of the third element is releasably connected to the second member. In still another more particular embodiment, rotation of the actuation knob when in the first state is effective to move first member relative to the second member to radially expand the frame to the expanded state; and rotation of the actuation knob when in the second state is effective to retract the distal end portion of the first element from between the first and second members to allow the locking features to engage each other and retain the frame in the expanded state and to release the frame from the second and third elements.

Also provided is an exemplary method comprising rotating an actuation knob situated of a medical device assembly to move first and second elements of the medical device assembly relative to a third element of the medical device assembly, wherein such rotating occurs in a first operation state of the medical device assembly, actuating a toggle to toggle the actuation knob from the first operation state to a second operation state, and after actuating the toggle, further rotating the actuation knob to move the first element relative to the second and third elements.

The method may further comprise actuating the toggle to move the toggle relative to the actuation knob from a first toggle position to a second toggle position to toggle the actuation knob from the first operation state to the second operation state.

The method may further comprise that the toggle comprises a knob, and actuating the toggle comprises rotating the knob in a first direction to move the toggle from a first toggle position to a second toggle position.

The method may further comprise actuating the actuation knob in a first operation state by rotating the knob in a first direction to expand a prosthetic medical device from a radially collapsed state to a radially expanded state, and rotating the knob in a second direction to radially collapse the prosthetic medical device.

The method may further comprise actuating the actuation knob in a second operation state by rotating the knob to lock the prosthetic medical device in the radially expanded state, and further rotating the knob to at least partially release the prosthetic medical device from delivery apparatus of the medical device assembly.

The method may further comprise actuating the actuation knob in a second operation state by rotating the knob to at least partially release the prosthetic medical device from the medical device delivery system.

The method may further comprise the prosthetic medical device being operatively coupled to the actuation knob by the first, second, and third elements and further that the act of rotating the actuation knob in the first operation state is effective to move the first and second elements axially relative to the third element to radially expand the prosthetic medical device.

The foregoing and other objects, features, and advantages of the invention will become more apparent from the following detailed description, which proceeds with reference to the accompanying figures.

BRIEF DESCRIPTION OF THE DRAWINGS

FIG. 16C is a cross-sectional view of the locking unit of FIG. 16A showing a release member retracted to release the locking unit from the delivery apparatus and lock the locking unit in the deployed state.

FIG. 16D is an enlarged cross-sectional view of a portion of the locking unit shown in FIG. 16C.

FIG. 19 illustrates a two-state actuation sequence for deploying a prosthetic frame assembly.

FIG. 20 is a perspective view of another embodiment of a delivery apparatus.

FIG. 27A is a side view of an alternative embodiment for a toggle mechanism, shown with a knob mechanism toggled into a first state.

FIG. 27B is a side view of the toggle mechanism of FIG. 27A, shown with the knob mechanism toggled into a second state.

DETAILED DESCRIPTION

Figure 1:
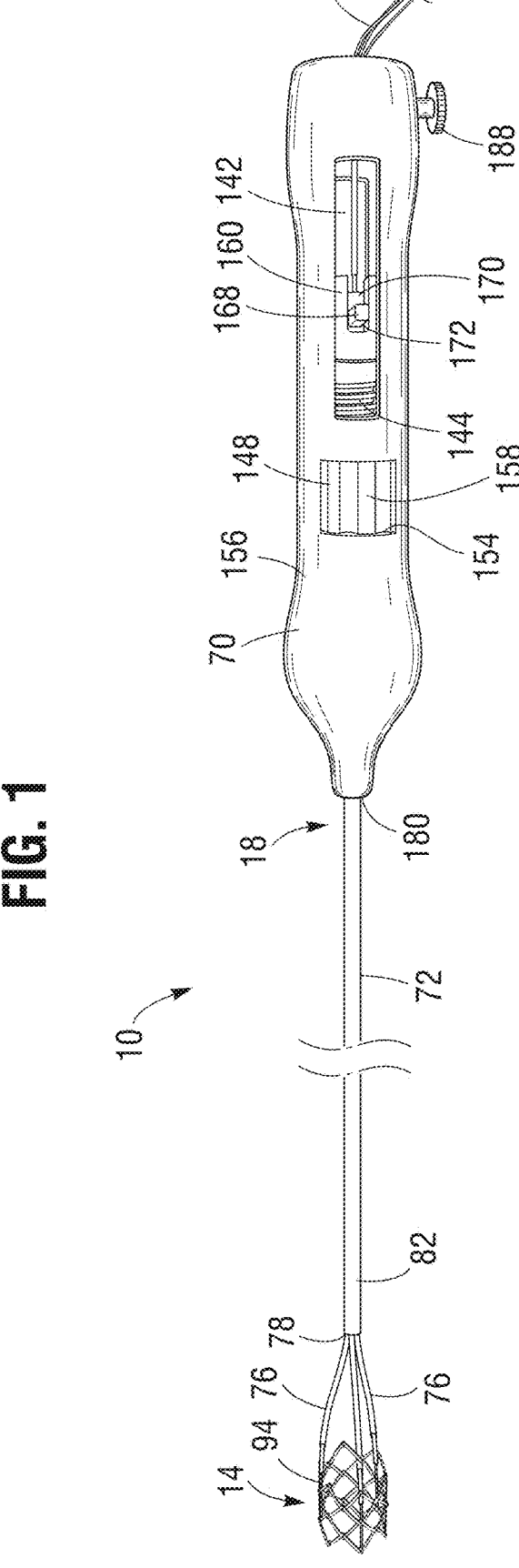
FIG. 1 is a side elevation view of an embodiment of a prosthetic valve delivery assembly.

FIG. 1 shows an example of a prosthetic implant delivery assembly 10 according to one embodiment of the present disclosure. The delivery assembly 10 can include two main components: a prosthetic heart valve 14 and a delivery apparatus 18. The prosthetic valve 14 can be releasably coupled to the delivery apparatus 18, as further described below. It should be understood that the delivery apparatus 18 and other delivery apparatuses disclosed herein can be used to implant prosthetic devices other than prosthetic valves, such as stents or grafts.

Figure 2:
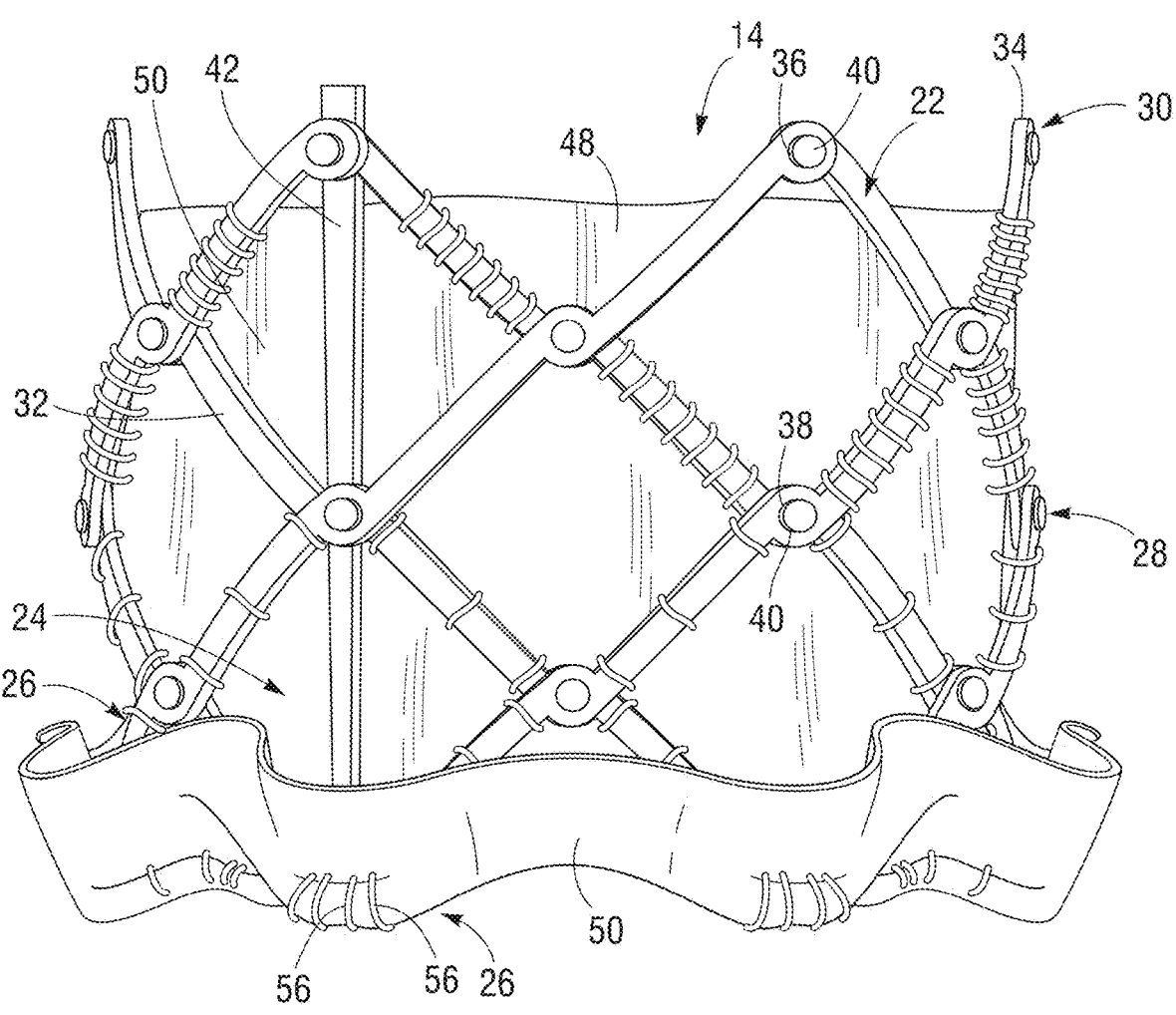
FIG. 2 is a side elevational view of a prosthetic valve, according to one embodiment.

FIG. 2 is a side elevational view of the prosthetic valve 14 shown in its deployed, radially expanded configuration. While only one side the prosthetic valve 14 is shown in the drawings, it should be appreciated that the opposite side is similar to the portion shown. The prosthetic valve 14 can include an annular stent or frame 22, and a valve structure 24 which can be coupled to the frame 22. The frame 22 can have an inflow end portion 26, an intermediate portion 28, and an outflow end portion 30. The prosthetic valve 14 can define a longitudinal axis extending through the inflow end portion 26 and the outflow end portion 30.

The frame 22 can be made of any of various suitable materials, such as stainless steel or a nickel titanium alloy ("NiTi"), for example Nitinol. The frame 22 can include a plurality of interconnected lattice struts 32 arranged in a lattice-type pattern and forming a plurality of apices 34 at the outflow end 30 of the prosthetic valve 14. The struts 32 can also form similar apices at the inflow end of the prosthetic valve (which are covered by a skirt 50 in FIG. 2). The lattice struts 32 are shown as positioned diagonally, or offset at an angle relative to, and radially offset from, the longitudinal axis of the prosthetic valve. In other implementations, the lattice struts 32 can be offset by a different amount than depicted in FIG. 2, or some or all of the lattice struts 32 can be positioned parallel to the longitudinal axis of the prosthetic valve 14.

The lattice struts 32 can be pivotably coupled to one another. In the illustrated embodiment, for example, the end portions of the struts 32 forming the apices 34 at the outflow end 30 and at the inflow end 26 of the frame 22 can have a respective opening 36. The struts 32 also can be formed with apertures 38 spaced apart along their lengths between the opposite ends of the struts. Respective hinges can be formed at the apices 34 and at the locations where struts 32 overlap each other between the ends of the frame via fasteners 40, which can comprise rivets or pins, that extend through the apertures 36, 38. The hinges can allow the struts 32 to pivot relative to one another as the frame 22 is expanded or contracted, such as during assembly, preparation, or implantation of the prosthetic valve 14. For example, the frame 22 (and thus the prosthetic valve 14) can manipulated into a radially compressed or contracted configuration (see, e.g., FIGS. 6 and 7) and inserted into a patient for implantation. Once inside the body, the prosthetic valve 14 can be manipulated into an expanded state (e.g., FIGS. 2 and 4) and then released from the delivery apparatus 18 (e.g., FIG. 1), as further described below.

The frame 22 can be formed using any suitable technique. Suitable techniques can include separately forming individual components (e.g., the struts 32 and fasteners 40) of the frame and then mechanically assembling and connecting the individual components to form the frame 22. The struts and fasteners can be formed, for example, by laser cutting those components from sheets or tubes of metal, or by electroforming (electroplating or electrodeposition) or physical vapor deposition. In some embodiments, electroforming or physical vapor deposition can be used to form subcomponents of the frame 22 or the entire frame 22 with pivotable connections between the struts In one implementation, for example, electroforming or physical vapor deposition can be used to form struts 32 having integral fasteners 40. The individual struts can be assembled together into a frame by inserting the integral fasteners 40 of each strut through a corresponding aperture of an adjacent strut. In some embodiments, electroforming or physical vapor deposition can be used to form the entire frame in its final, cylindrical shape. In other embodiments, electroforming or physical vapor deposition can be used to form the entire frame in a flattened configuration, after which the ends of the flattened frame are connected to each other to form the final cylindrical shape of the frame.

In other embodiments, the lattice struts 32 are not coupled to each with respective hinges (e.g., fasteners 40) but are otherwise pivotable or bendable relative to each other to permit radial expansion and contraction of the frame. For example, the frame 22 can be formed (e.g., via laser cutting, electroforming or physical vapor deposition) from a single piece of material (e.g., a metal tube).

In addition to the lattice struts 32, the frame 22 can include one or more longitudinally extending support struts 42. The support struts 42 can be circumferentially spaced about the frame 22 and coupled, including being pivotally coupled, to the lattice struts 32. The support struts 42 can be positioned parallel to, and radially spaced apart from, the longitudinal axis of the prosthetic valve. The support struts 42 can enhance the rigidity to the frame 22 and help the frame 22 maintain a uniform shape as it is expanded or contracted. In some implementations, the frame 22 does not include the support struts 42. The support struts 42 can be connected to the lattice struts 32 at the hinge joints formed by fasteners 40 that can extend through respective apertures in the lattice struts and the support struts.

Figures 3, 4, 5:
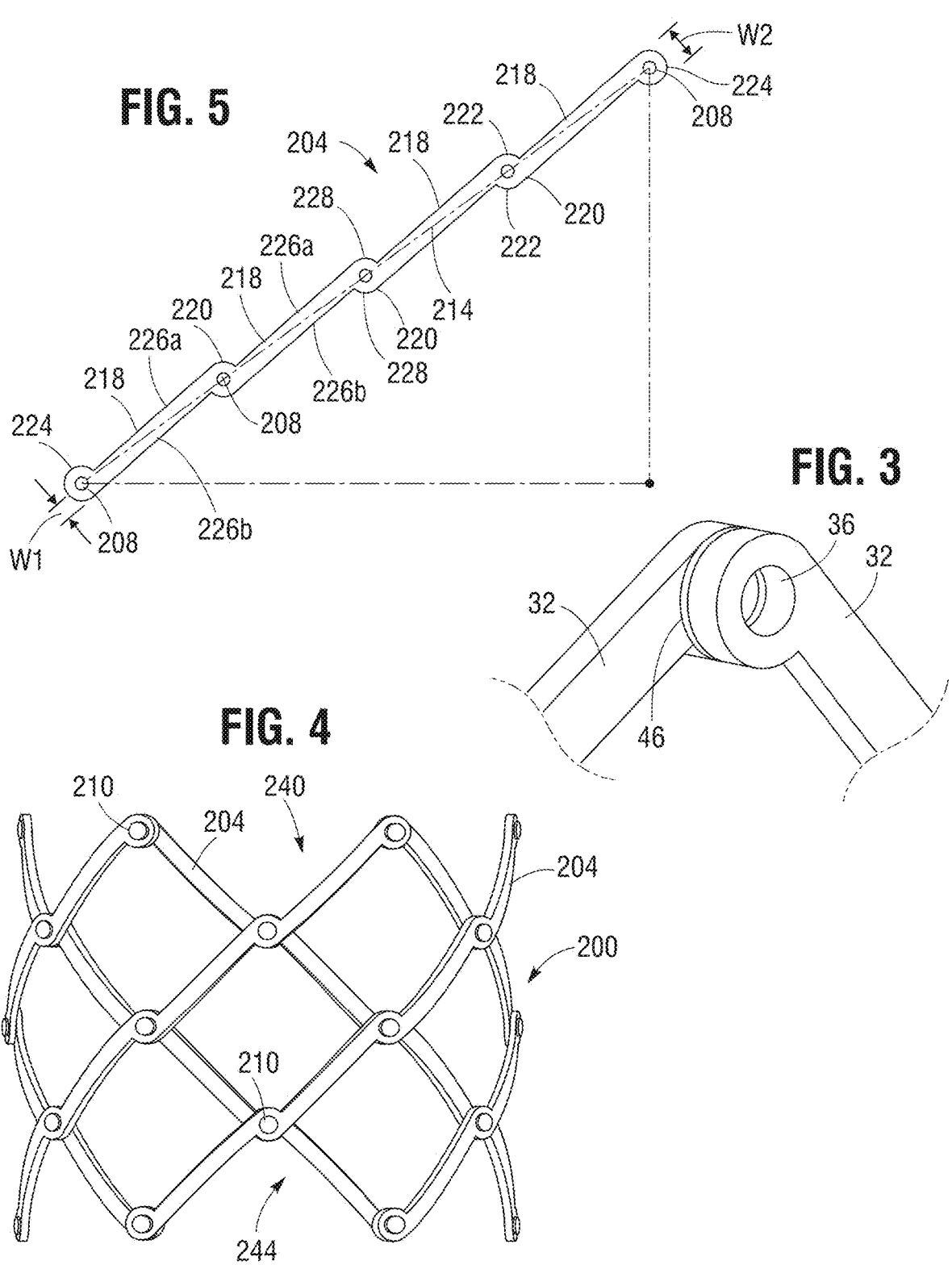
FIG. 3 is an enlarged perspective view of an embodiment of coupled frame struts useable in the prosthetic valve of FIG. 2.
FIG. 4 is a side elevational view of another embodiment of a frame that can be used in the prosthetic valve of FIG. 2.
FIG. 5 is a side view of an embodiment of a strut for a frame of a prosthetic valve, such as the frame of FIG. 2, or the frame of the FIG. 4.

With reference to FIG. 3, a spacer 46, such as a washer or bushing, can be disposed in a joint between lattice struts 32, or a joint between lattice struts 32 and support struts 42 (not shown). When the lattice struts 32 and/or support struts 42 are pivotally coupled to one another, the spacers 46 can assist the lattice struts 32, or lattice struts 32 and support struts 42, in moving relative to one another. The spacer 46 can also act to space the lattice struts 32 from one another, or from the support struts 42. In some implementations, the frame 22 does not include the spacers 46, or the lattice struts 32, or lattice struts 32 and support struts 42, are spaced apart in a different manner Returning to FIG. 2, the prosthetic valve 14 can include a valvular structure 24 to regular the flow of blood through the prosthetic valve. The valvular structure 24 can comprise, for example, a leaflet assembly 48 comprising one or more leaflets made of a flexible material. The leaflets of the leaflet assembly 48 can be made from in whole or part, biological material (e.g., pericardial tissue, such as bovine or equine pericardium), biocompatible synthetic materials, or other such materials, such as those described in U.S. Pat. No. 6,730,118, which is incorporated herein by reference.

The prosthetic valve can also include an annular skirt or sealing member 50 that can be secured to the outer surface of the inflow end portion 26 of the frame 22, for example, with sutures 56 adjacent the inflow end portion 26 of the frame 22. The inflow end portion of the leaflet assembly 48 can be secured to the frame 22 and/or the skirt 50, for example using sutures 56. The skirt 50 helps establish a seal with the native tissue at the implantation site to prevent or minimize paravalvular leakage. In alternative embodiments, the prosthetic valve can have a skirt or sealing member mounted on the inside of the frame or a skirt or sealing member mounted on the inside and outside of the frame. The skirt can be formed from natural tissue (e.g., pericardial tissue) or any of various biocompatible synthetic materials, including biocompatible fabrics (e.g., polyethylene tereph-thalate (PET) fabric).

Further details regarding transcatheter prosthetic heart valves, including the manner in which the valve structure 24 can be coupled to the frame 22 of the prosthetic valve 14, can be found, for example, in U.S. Pat. Nos. 6,730,118, 7,393,360, 7,510,575, 7,993,394, and 8,652,202, which are incorporated herein by reference in their entireties.

FIG. 4 is a side elevational view of a portion of a frame 200 that can be used with a prosthetic valve in at least certain embodiments of the present disclosure. While only one side of the frame 200 is depicted in FIG. 4, it should be appreciated that the opposite side can be similar to the portion shown. The frame 200 is similar to the frame 22 discussed above but does not include the longitudinal struts 42. The frame 200 can include a plurality of lattice struts 204. Each of the lattice struts 204 can include a plurality of apertures 208. The apertures 208 can be used to connect the lattice struts 204 to one another using fasteners 210, such as described above for the lattice struts 32 (FIG. 2). In other implementations, the apertures 208 and fasteners 210 can be omitted. For example, the lattice struts 204 can be fixedly connected to one another, such as by welding or adhesion, or by laser-cutting the individual struts of the frame from a metal tube. Although not shown in FIG. 4, a spacer may be included between the lattice struts 204, such as intermediate the portions of the lattice struts 204 having the apertures 208. In a particular example, the spacers can be configured as described above for the spacer 46 Similarly, if desired, the frame 200 can include support struts (not shown) that can be analogous to the support struts 42 (FIG. 2).

As best shown in FIG. 5, each lattice strut 204 can have an offset, or zig-zag, pattern defined by a plurality of offset linear portions or segments 218. The linear segments 218 in the illustrated embodiment are arranged end-to-end relative to each other with adjacent ends interconnected to each other by intermediate segments 220. The strut 204 can have enlarged end portions 224 that form the apices at the inflow and outflow end of the frame. Each linear segment 218 is slightly laterally offset from an adjacent linear segment 218 in a direction perpendicular to the overall length of the strut 204 to provide the zig-zag pattern to the strut. Each of the intermediate segments 220 and end portions 224 can have a respective aperture 208 at its geometric center for receiving a fastener 210.

The amount of offset of each linear segment 218 relative to an adjacent linear segment along the length of the strut 204 can be constant such that an imaginary line 214 can pass through the aperture 208 of each intermediate segment 220 along the entire length of the strut. In alternative embodiments, the amount of offset between two adjacent linear segments 218 can vary along the length of the strut. For example, the amount of offset between linear segments 218 adjacent the outflow end of the frame can be greater than the amount of offset between linear segments 218 adjacent the inflow end of the frame, or vice versa.

The linear segments 218 can include at least substantially flat or linear opposing longitudinal edges 226a, 226b extending between curved or rounded edges 228 of the intermediate segments 220. In alternative embodiments, the opposing edges 228 of the intermediate segments 220 can be substantially flat or linear edges that extend at an angle between respective ends of the edges 226a, 226b of the liner segments 218.

As best shown in FIG. 5, the width W1 of each liner segment 218 is defined as the distance measured between the opposing edges 226a, 226b of a segment 218. In the illus-trated embodiment, the width W1 is constant along the length of the strut 204. As such, each longitudinal edge 226a is laterally offset from an adjacent longitudinal edge 226a of an adjacent linear segment 218, and each longitudinal edge 226b is laterally offset from an adjacent longitudinal edge 226b of an adjacent linear segment 218. The width W2 of each intermediate segment 220 and end portion 224 can be greater than the width W1 of the linear segments 218.

In alternative embodiments, the width W1 of each linear segment 218 can vary along the length of a strut. For example, the width W1 of a linear segment 218 adjacent the inflow end of the frame can be greater than the width W1 of a linear segment 218 adjacent the outflow end of the frame, or vice versa. Further, where the width W1 of the linear segments 218 vary along the length of a strut 204, a linear segment can have one longitudinal edge 226a or 226b that is collinear with a longitudinal edge of an adjacent linear segment on the same side of the strut, while the other longitudinal edge 226a, 226b is laterally offset from the longitudinal edge of an adjacent linear strut on the same side of the strut. In other words, the strut 204 can have an overall zig-zag or offset pattern by virtue of the varying widths W1 of the linear segments.

Figure 6:
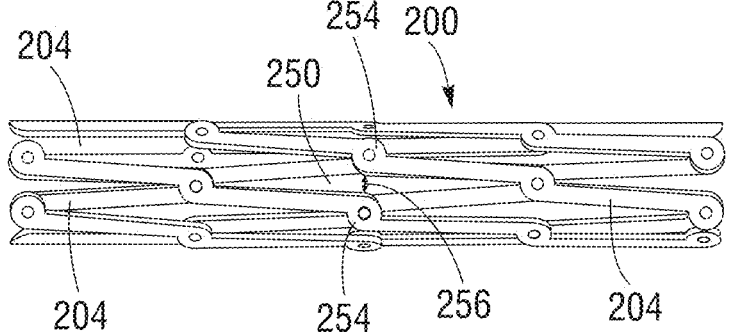
FIG. 6 is a side view of the frame of FIG. 4 shown in a radially compressed state.
Figure 7:
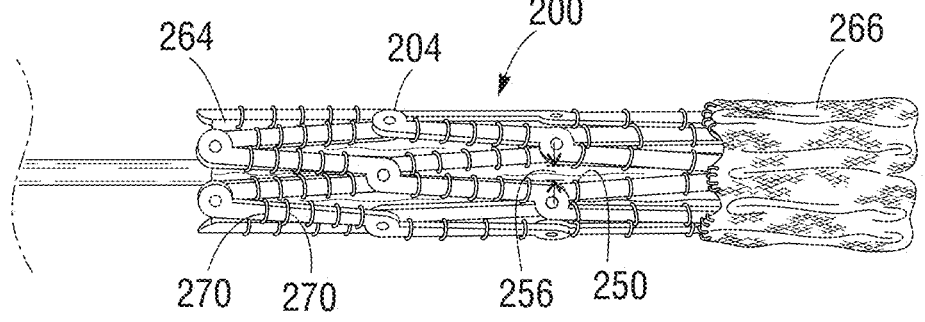
FIG. 7 is a side view of a prosthetic valve incorporating the frame of FIG. 4 shown in a radially compressed state.

The offset, or zig-zag, pattern of the strut segments 218 can help space apart the struts 204 in the circumferential direction when the frame 200 is in a radially compressed state, as shown in FIGS. 6 and 7. As shown, the open lattice structure of the frame 200 defining open cells 250 between the struts 204 can be preserved even when the frame 200 is fully compressed or contracted. For example, with reference to FIG. 6, although the width of the cells 250 along the length of the frame 200 can between adjacent struts, a gap 256 remains at the middle of a cell 250 between two adjacent pivot joints 254.

When the frame 200 is incorporated in a prosthetic valve (e.g., the prosthetic valve 14), the spaced-apart nature of the struts 204, including the gaps 256, can assist in protecting the soft components of the prosthetic valve as the frame 200 is expanded and contracted. FIG. 7, for example, shows a prosthetic valve comprising the frame 200, a skirt 266 mounted on the outside of the frame 200 and a leaflet assembly 264 mounted inside of the frame 200. An inner skirt (not shown) also can be mounted inside of the frame. The skirt 266 and leaflet assembly 264 can be coupled to the frame 200, such as with sutures 270. The sutures 270 can extend through the material of the skirt 266 and/or the leaflet assembly 264 and radially about the struts 204. The gaps 256 created by the offset configuration of the struts 204 can protect the leaflets 264, the skirt 266, and/or the sutures 270 from being pinched or sheared between adjacent struts 204 when the prosthetic valve is radially compressed. In this manner, the soft components of the prosthetic valve are protected against damage that can occur from contact with the metal struts of the frame.

The delivery apparatus 18 of FIG. 1 is particularly suited for implanting the prosthetic valve 14 or any of the other prosthetic valves disclosed herein. However, it should be noted that any of the prosthetic valves disclosed herein can be implanted using other suitable delivery apparatuses. For example, any of the prosthetic valves disclosed herein can be crimped over an inflatable balloon of a conventional balloon catheter. Once delivered to the implantation site, the balloon can be inflated to expand the prosthetic valve to its fully functional size.

Referring again to FIG. 1, the delivery apparatus 18 can include a handle 70, an elongate shaft 72 extending distally from the handle 70, a plurality of first actuation members 76 (also referred to as elongate positioning members), such as in the form of positioning tubes, extending through the shaft and distally outwardly from a distal end 78 of the shaft 72, a plurality of release members 106 (FIG. 9) extending through respective positioning members 76, and a plurality of second actuation members 86 (also referred to as "teth-ers") extending through respective release members 106. The positioning members 76 can be at least partially disposed radially within, and extend axially through, one or more lumens of the shaft 72. For example, the positioning members 76 can extend through a central lumen of the shaft 72 or through separate respective lumens formed in the shaft 72.

Figure 13:
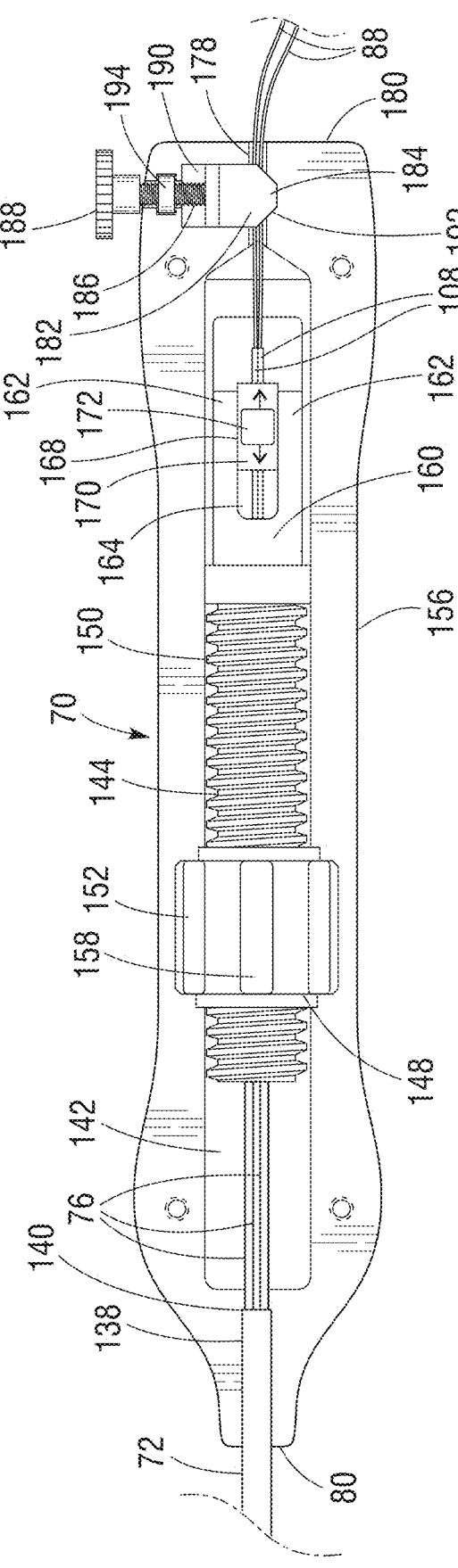
FIG. 13 is an enlarged cross-sectional view of the handle of the prosthetic valve delivery assembly of FIG. 1.

The shaft 72 can have a distal end portion 82 that can function as a sheath for containing or housing the prosthetic valve 14 in a radially compressed state for delivery through a patient's vasculature. In this regard, the distal end portion 82 can have a lumen that is sized to receive the prosthetic valve 14 in a radially compressed state. As shown in FIG. 13, the proximal end portion of the shaft 72 can extend into an axially extending bore 138 formed in the distal end portion of the handle 70. The proximal end portion of the shaft 72 can be retained within the axial bore 138 through pressure or frictional contact with the bore 138, using an adhesive, a clamp, a fastener, by thermally bonding the catheter 72 to the bore 138, or by some other technique or mechanism.

Figures 8, 9:
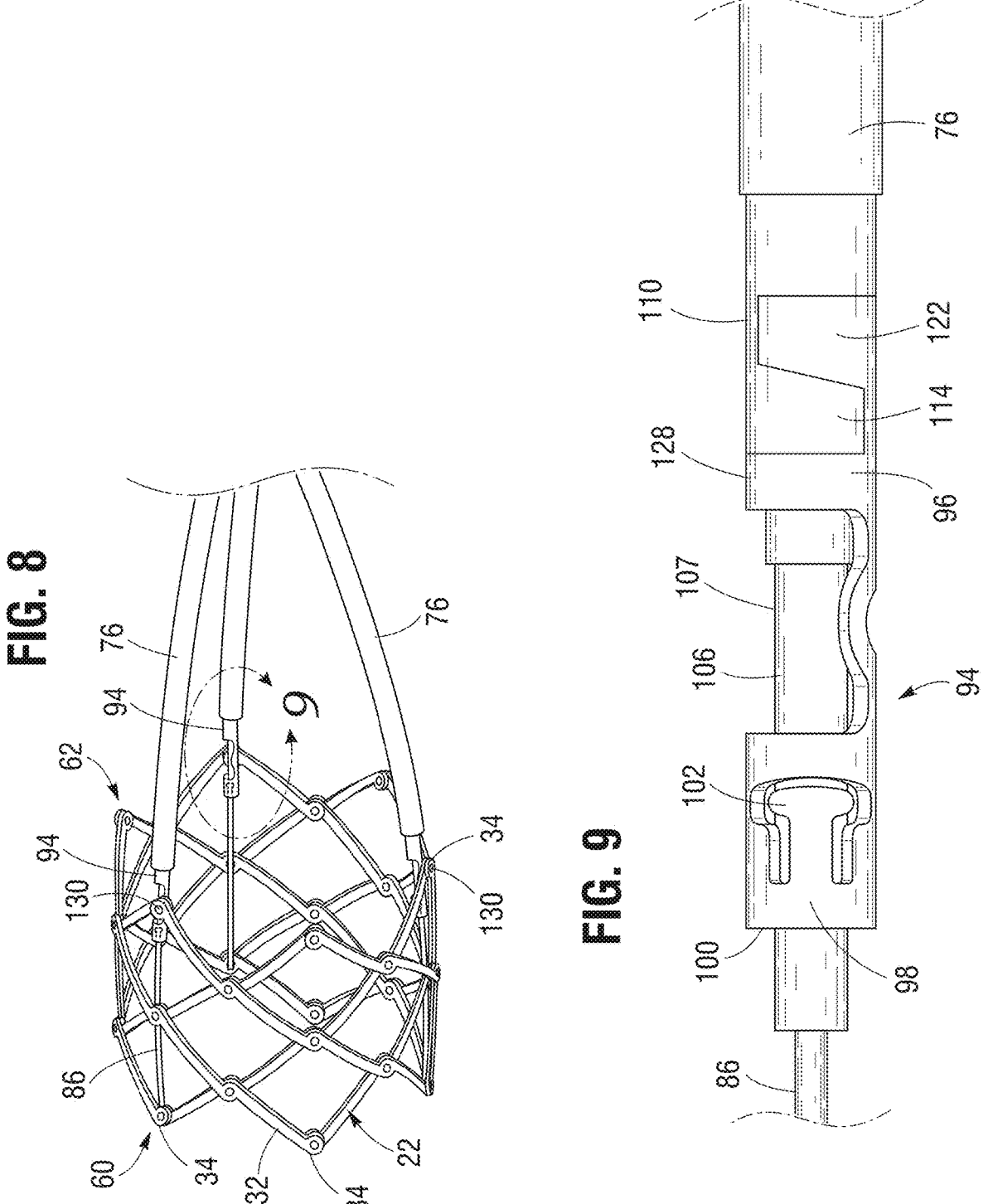
FIG. 8 is an enlarged perspective view of the distal end portion of the prosthetic valve delivery assembly of FIG. 1.
FIG. 9 is an enlarged side view of a locking unit and the distal end portion of a positioning member of the prosthetic valve delivery assembly of FIG. 1.

The positioning members 76 have distal end portions that can be releasably connected to the prosthetic valve 14 via respective release-and-locking units 94 (as best shown in FIG. 8). As shown in FIG. 13, the positioning members 76 can extend through the shaft 72, and proximally beyond a proximal end 140 of the shaft, and into a central bore 142 of the handle 70. A lead screw 144 can be disposed within the central bore 142 of the handle 70. The proximal ends of the positioning members 76 can be secured to the lead screw 144, such as being received within a bore (not shown) of the lead screw 144, where they can be secured by pressure or frictional contact with the bore of the lead screw 144, using an adhesive, a clamp, a fastener, thermal bonding, or another suitable technique or mechanism.

As shown in FIGS. 8 and 9, each actuation member 86 can extend through a lumen of a respective positioning member 76. The actuation members 86 can be coupled at their distal end portions to the distal end 60 of the frame 22. For example, the distal end portion of each actuation member 86 can be connected to an apex 34 at the distal end 60 of the frame, such as by welding, an adhesive, or a mechanical fastener. Each actuation member 86 can also extend through a lumen of a respective locking unit 94 that can be coupled to the frame 22, such as to an apex 34 at a proximal end 62 of the frame. The actuation members 86 can extend proxi-mally into and through the handle 70. Proximal end portions 88 of the actuation members 86 can be releasably retained by a clamping member 182 mounted in or on the handle 70 (FIG. 13).

The actuation members 86 function to apply a proximally directed pulling force to the distal end 60 of the frame in cooperation with the positioning members 76 that apply a distally directed pushing force to the proximal end 62 of the frame to effect radially expansion of the frame 22. In particular embodiments, the actuation members 86 can com-prise a relatively flexible but relatively non-elastic material that can effectively transfer pulling forces generated at the handle 70 to the distal end of the frame 22. For example, the actuation members 86 can comprise wires, sutures, strings, or similar materials. In other embodiments, the actuation members 86 can be relatively stiffer component, such as shaft or rod, that can transfer proximally directed pulling forces to the frame as well as distally directed pushing forces to the frame.

The release members 106 have distal end portions 107 that extend coaxially through respective locking units 94 (FIG. 9) and proximal end portions 108 that extend into the handle 70 (FIG. 13). The proximal end portions 108 of the release members 106 can extend through the lead screw 144 and can be secured to a release knob 168 within the handle 70.

Referring to FIGS. 1 and 13, a threaded actuator nut 148 can be disposed about the lead screw 144. Internal threads (not shown) of the threaded actuator nut 148 can engage threads 150 of the lead screw 144. An outer surface 152 of the threaded actuator nut 148 can extend through an aperture or window 154 formed in the outer surface 156 of the handle 70. The outer surface 152 of the threaded actuator nut 148 can include a texture, such as ridges 158, to aid a user in grasping and rotating the threaded actuator nut 148.

Rotation of the threaded actuator nut 148 in a first direction can cause the lead screw 144 to translate axially in the distal direction relative to the handle 70, thereby causing the positioning members 76 to translate distally through the lumen of the shaft 72. Rotation of the threaded actuator nut 148 in the opposite direction can cause the lead screw 144 to translate proximally relative to the handle, thereby causing the positioning members 72 to retract or translate proximally through the lumen of the shaft 72.

In particular implementations, the number and spacing of the threads 150 of the lead screw 144 (and thus the mating threads of the threaded actuator nut 148), and the axial length of the lead screw 144, can be selected to provide a desired degree of travel for the positioning members 76 and the release members 106. For example, the desired degree of travel can be sufficient to allow the frame 22 (and thus the prosthetic valve 14) to be manipulated between a fully expanded state (such as shown in FIGS. 2 and 8) and a fully contracted or compressed state (such as shown in FIGS. 6 and 7), including states in between being fully compressed or contracted and fully expanded, as further described below.

The release-and-locking units 94 (also referred to as "locking units") in the illustrated embodiment are configured to releasably connect the positioning members 76 to the frame 22 of the prosthetic valve 14 and to selectively secure the actuation members 86 to retain the prosthetic valve 14 in a deployed and expanded state. With reference to FIGS. 8-11, the locking units 94 can comprise a generally cylindrical body 96, which can be secured to the frame 22 of the prosthetic valve 14 by a fastener 130 (e.g., a pin or rivet). The fastener 130 can extend through an aperture 132 (FIG. 11) formed in the body 96 and through one or more corresponding apertures 36 in the frame struts 32 forming the apices 34 of the frame (FIG. 8).

Figures 10A, 10B, 11:
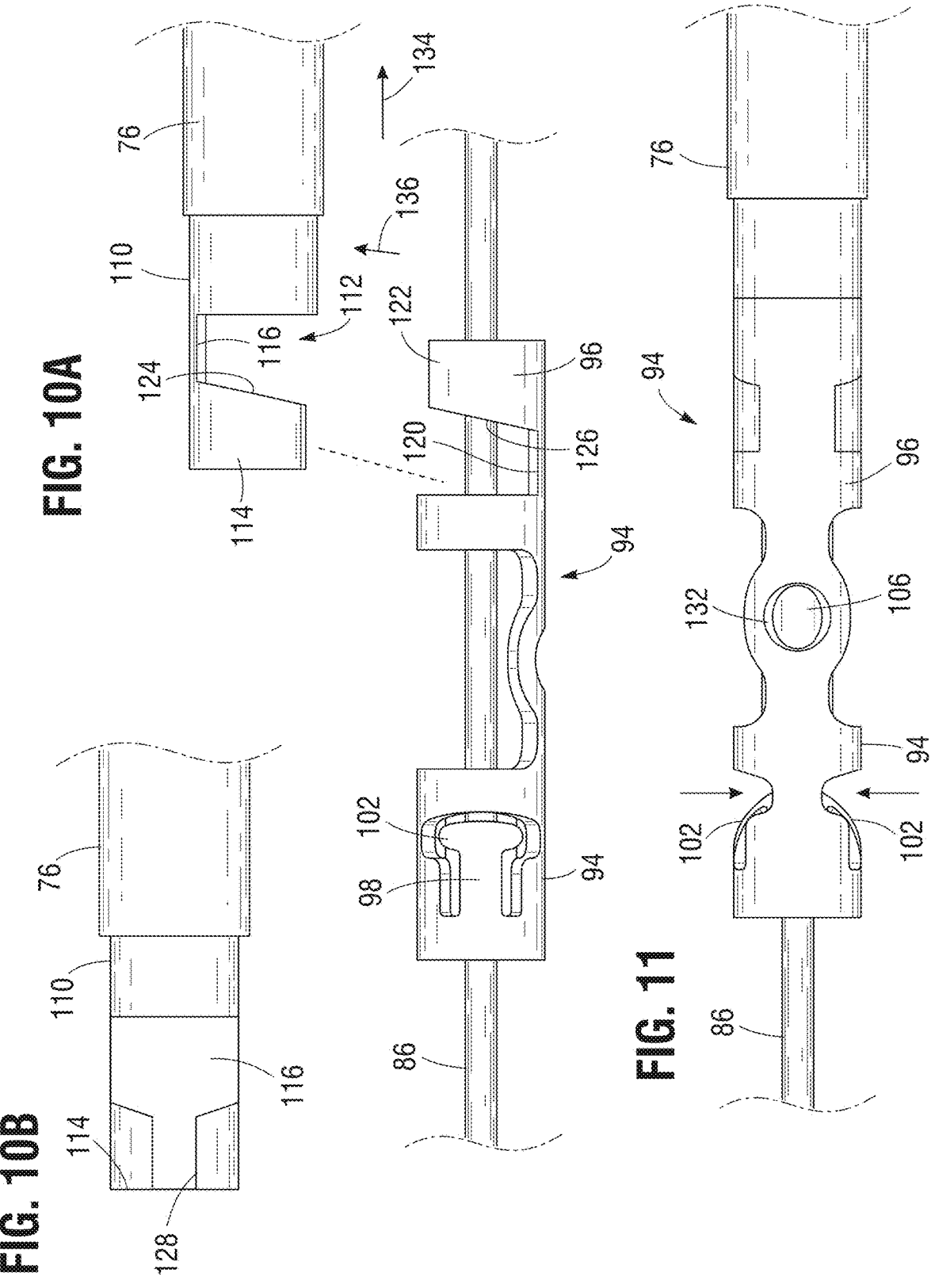
FIG. 10A is an enlarged side view of the locking and the positioning member of FIG. 9, illustrating the positioning member decoupled from the locking unit.
FIG. 10B is enlarged side view of the distal end portion of the positioning member of FIG. 10A rotated 90 degrees from the orientation shown in FIG. 10A.
FIG. 11 is an enlarged side view of the locking unit and the positioning member of FIG. 9 rotated 90 degrees from the orientation shown in FIG. 9.

The body 94 can comprise a locking feature, such as in the form of a clamp 98, disposed adjacent a distal end 100 of the locking unit 94 for selectively engaging an actuation member 86. The clamp 98 can comprise, for example, a pair of diametrically opposed jaws 102 that are biased radially inwardly toward each other (as best shown in FIG. 11). A release member 106 can be disposed within a lumen of each locking unit 94 to retain the jaws 102 of the clamp in a non-engaged or non-locking state during delivery of the prosthetic valve 14 (FIG. 9). Each release member 106 can extend proximally through a respective positioning member 76 to the handle 70. As discussed above, the proximal end portions 108 of the release members can be secured to a release knob 168 in the handle (FIG. 13). Each actuation member 86 can extend proximally through a lumen of a respective release member 106 into the handle 70.

In particular implementations, the release members 106 can be made from any suitable biocompatible metallic material or a polymeric material. In least some examples, the material can be selected to allow the release members 106 to be easily moveable relative to the jaws 102 during valve deployment, as further described below. For example, the release members 106 can be made from a lubricious or low friction material (e.g., PTFE) or can have an outer layer made from a lubricious or low friction material (e.g., PTFE).

When the release members 106 are disposed within the locking units 94 extending between the jaws 102, the jaws 102 are held in an unlocked stated and are prevented from contacting the actuation members 86. In the unlocked state, the actuation members 86 and the positioning members 76 can move freely in the axial direction with respect to one another to control radial expansion and compression of the prosthetic valve 14. When the prosthetic valve 14 is to be released from the delivery apparatus 18, the release members 106 can be retracted proximally relative to the locking units 94 and the positioning members 76. As shown in FIGS. 10A and 11, once the release members 106 are removed from engagement with the jaws 102, the jaws 102 can move to a locked or engaged state engaging the actuation members 86, thus securing the actuation members 86 from further axial movement, thus retaining the frame 22 of the prosthetic valve 14 in a desired expanded state.

Referring back to FIG. 10, the locking units 94 can be releasably coupled to the positioning members 76 by the release members 106. In the illustrated embodiment, for example, a distal end portion 110 of each positioning member 76 can include a coupling portion 112 that can include a tab 114 and a notch 116. Each locking unit 94 can include a corresponding notch 120 configured to receive the tab 114 of the positioning member 76. Similarly, each locking unit 94 can include a tab 122 to be inserted into, and received by, the notch 116 of a respective positioning member 76. The tabs 114,122 and notches 120, 116, along with the release member 106, collectively can form a releasable, interlocking joint. The engagement of the tabs 114, 122 with the notches 120, 116 prevent axial separation of the positioning member 76 from the locking unit 94, while the release member 106, which extends through the tabs 114, 122 in the locked state, prevents lateral separation of the positioning member 76 from the locking unit 94.

As shown in FIG. 10B, the tab 114 of the positioning member 76 can include an axially extending slot 128. The slot 128 can be sized to allow the tab 114 to be placed around the actuation member 86 or removed from the actuation member 86 by passing the actuation through the slot 128. However, the slot 128 desirably is narrower than the diameter of the release member 106 to prevent lateral separation of the positioning member 76 from the locking unit 94 when the release member 106 is in a position extending through the tabs 114, 122 as depicted in FIG. 9. As noted above, retraction of the release member 106 from the jaws 102 of the clamp 98 allows the jaws to engage the actuation member 86. Further retraction of the release member 106 until the distal end of the release member 106 is proximal to the tab 122 and the notch 116 allows the distal end portion 110 of the positioning member 76 to be separated from the locking unit 94 in a lateral direction (in a direction perpendicular to the length of the locking unit and the positioning member), as depicted in FIG. 10A. As the positioning member 76 moves in a lateral direction away from the locking unit 94, the actuation member 86 can pass through the slot 128 in the tab 114.

As further shown in FIG. 10A, the tabs 114, 122 can be formed with respective inclined cam surfaces 124, 126, respectively, to facilitate the separation of the positioning member 76 from the locking unit 94. Each cam surface 124, 126 is inclined relative to the longitudinal axis of the positioning member 76 at angle less than 90 degrees. As such, applying a proximally directed force to the positioning member 76 in the direction of arrow 134 (such as by applying a pulling force to the positioning member at handle 70) causes the positioning member 76 to slide laterally away from the locking unit 94 in the direction of arrow 136.

The locking units 94 and/or the positioning members 76 can include a cutting mechanism to cut the portions of the actuation members 86 that extends proximally beyond the jaws 102 of the clamps 98 after the prosthetic valve is expanded and the release members are retracting to actuate the clamps. For example, a blade, or other cutting surface, can be placed across the slot 128, such that the actuation members 86 can be severed when they pass through the slot 128 during lateral separation of the positioning member 76 away from the locking unit 94.

In another example, the locking units 94 can include a clamping member that can include cutting jaws (such as sharpened or serrated jaws) positioning proximal to the jaws 102. The cutting jaws, like the jaws 102, can be retained in an open position away from the actuation member by the release member 106. When the release member 106 is retracted out of engagement with the cutting jaws, the cutting jaws can deflect radially inwardly against the actuation member 86, thereby severing it at that location. In further examples, a separate cutting device can be used to sever the actuation members 86 at a desired location after the positioning members 76 are released from the prosthetic valve 14, and optionally, after the delivery apparatus 18 is removed from the body.

Referring again to FIGS. 1 and 13, the lead screw 144 includes an extension portion 160 that extends proximally from the threaded portion of the lead screw. The extension portion 160 can comprise two leg portions 162 defining a U-shaped aperture or slot 164 between the leg portions 162. The release knob 168 can comprise a slidable member 170 disposed between the leg portions 162 and a user-engageable portion 172 extending radially outwardly from the slidable member 170. The proximal end portions 108 of the release members 106 can be fixedly secured to the slidable member 170, such as with a suitable adhesive, such that axial movement of the slidable member 170 in the distal and proximal directions causes corresponding movement of the release members.

The release knob 168 can be configured to be movable with, and also independently of, the lead screw 144. As noted above, axial movement of the lead screw 144 causes corresponding movement of the positioning members 76. Thus, when the release knob 168 is retained relative to the extension portion 160 of the lead screw 144, axial movement of the lead screw 144 causes the release knob 168 and the release members 106 to move with the positioning members 76, such as during deployment and expansion of the prosthetic valve. When the release knob 168 is not retained relative to the extension portion 160 of the lead screw 144, the release knob 168 can be translated axially relative to the extension portion, thereby effecting axial movement of the release members 106 relative to the positioning members 76 to actuate the clamping mechanism 98 of the locking unit 94 and release the positioning members 76 from the frame 22 of the prosthetic valve.

Various mechanisms can be used to selectively and releasably retain the release knob 168 axially relative to the extension portion 160 of the lead screw 144. For example, a moveable pin or similar mechanism can be inserted through the slidable member 170 and one or both leg portions 162 of the extension portion 160 to retain the axial position of the slidable member 170 relative to the lead screw 144. Removing the pin from the slidable member 170 and/or the leg portions 162 allows axial movement of the release knob 168 relative to the lead screw.

In another embodiment, the slidable member 170 can be configured to move between a first position where it is frictionally engaged by the extension portion 160 and a second position where the slidable member 170 is no longer frictionally engaged by the extension portion 160. In the first position, the axial movement of the lead screw 144 causes corresponding movement of the release knob 168. In the second position, the release knob 168 can be moved axially independently of the lead screw 144 in the distal and proximal directions.

The actuation members 86 can extend proximally beyond the proximal end portions 108 of the release members 106 and through an axially extending bore or opening 178 formed in the proximal end portion 180 of the handle 70. The actuation members 86 can be selectively secured relative to the handle 70 using a clamping, or retaining, mechanism 182. The retaining mechanism 182 can comprise a plug member 184, a screw member 186 connected at one end of the plug member 184, and knob 188 connected to the opposite end of the screw member 186. The plug member 184 can be positioned in a radially bore 184 formed in the proximal end portion 180 of the handle 70. The plug member 184 can include a triangular or trapezoidal lower surface that can be placed in, and removed from, contact with a corresponding shaped surface 192 of the radial bore 190. In other implementations, the plug member 184 can have a different shape. The screw member 186 extends through a captured nut 194 such that rotation of the knob 188 causes the plug member 184 to move toward or away from the surface 192 of the radial bore 190.

When the knob 188 is fully tightened (such as by rotating the knob 188 in a first direction), the lower surface of the plug member 184 can clamp the actuation members 86 against the surface 192, thereby securing the actuation members 86 against movement relative to the handle 70, the shaft 72, the locking units 94, and the frame 22 of the prosthetic valve. When the knob 190 is rotated in the opposite direction, the plug member 184 can move away from the surface 192 and the actuation members 86, allowing the actuation members to move relative to the handle 70, the shaft 72, the locking units 94, and the frame 22 of the prosthetic valve.

To use the delivery apparatus 18 to delivery and implant the prosthetic valve 14 at a desired location within the heart (e.g., the native aortic valve), the prosthetic valve 14 is connected to the positioning members 76 using the locking units 94 and the release members 106, as shown in FIGS. 8 and 9. The release knob 168 is retained relative to the lead screw 144 to prevent relative movement between the positioning members 76 and the release members 106. The prosthetic valve 14 can then be radially compressed or crimped to a compressed state, as shown in FIG. 7. The compressed prosthetic valve 14 can be loaded into the sheath 82 of the shaft 72.

Conventional techniques and devices can be used to insert and advance the delivery apparatus 18 and the prosthetic valve 14 through a patient's vasculature to the desired implantation site. For example, a prosthetic aortic valve can be delivered in a retrograde approach by advancing the delivery apparatus through a femoral artery and the aorta to the native aortic valve. At or adjacent the implantation site, the prosthetic valve 14 can be deployed from the sheath 82 by rotating the actuator nut 148 in a direction to cause the lead screw 144 to move distally relative to the handle 70. This causes the positioning members 76 and the release members 106 to move distally relative to the shaft 72. The positioning members 76 push the prosthetic valve 14 distally relative to the shaft 72. The actuator nut 148 can be rotated until the prosthetic valve is deployed from the distal end of the sheath 82. In some implementations, the inherent resiliently of the frame 22 may cause the prosthetic valve to at least partially expand when advanced from the sheath 82.

As the prosthetic valve 14 is deployed from the sheath 82, the retaining mechanism 182 can be in a release position allowing the actuation members 86 to move distally with the prosthetic valve. In this manner, the actuation members 86 do not apply any expansion forces to the prosthetic valve as it is being deployed from the sheath. To apply an expansion force to the prosthetic valve, the retaining mechanism 182 is tightened to retain the actuation members 86 relative to the handle 70. Continued rotation of the actuator nut 148 causes the positioning members to continue to apply a distally directed force on the proximal end of the frame 22 while the actuation members 86 (which are now restrained by the retaining mechanism 182) become taught and apply a proximally directed force on the distal end of the frame 22. The application of these forces causes the frame 22 to foreshorten axially and expand radially.

In some embodiments, the retaining mechanism 182 can be kept in the locked or engaged position against the actuation members 86 during valve deployment so long as the actuation members are long enough and contain enough slack to avoid applying any expansion force on the prosthetic valve as it is advanced from the sheath 82. For example, the lengths of the actuation members 86 can be selected to avoid applying any expansion force on the prosthetic valve as it is advanced from the sheath 82 and after the prosthetic valve is fully deployed from the sheath, the actuation members 86 become taught and begin to apply an expansion force on the frame opposite the expansion force of the positioning members 76 to expand the prosthetic valve.

If re-positioning or complete withdrawal of the prosthetic valve from the body is required, the user can rotate the actuator nut 148 in the opposite direction, which causes the positioning members 76 to pull the prosthetic valve back into the sheath 82. The action of the distal end portions 110 of the positioning members 76 being retracted into the sheath 82 causes the prosthetic valve to compress radially. If desired or needed, the prosthetic valve can be partially compressed without being retracted into the sheath and then re-positioned and re-expanded by rotating the actuator nut 148. In some cases, the prosthetic valve can be completely retracted back into the sheath 82 for re-positioning or complete withdrawal of the prosthetic valve from the body.

Once the prosthetic valve is expanded and positioned at the desired location, the release members 106 can be retracted from the locking units 94. This can be accomplished by releasing the release knob 168 from the lead screw 144 and retracting the release knob 168 proximally, which causes the release members 106 to retract relative to the locking units 94. When the distal ends of the release members 106 are proximal to the jaws 102 of the clamping mechanism 98, the jaws can engage the actuation members 86 to retain the prosthetic valve in the expanded state. Further retraction of the release members 106 past the tabs 122 of the locking units 94 allows the positioning members 76 to be released from the locking units. Retraction of the positioning members 76 by rotation of the actuator nut 148 or retracting the handle 70 causes the distal end portions 110 of the positioning members to pull free of the locking units 94. As discussed above, the portions of the actuation members 86 proximal to the clamping mechanisms 98 can be severed and removed from the body. Thereafter, the delivery apparatus can be withdrawn from the body.

Figure 12A:
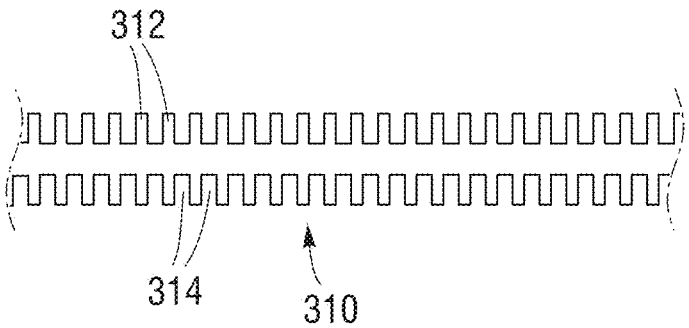
FIG. 12A is a schematic diagram of an actuation member having locking features that can be used with the prosthetic valve delivery assembly of FIG. 1, according to one embodiment.
Figure 12B:
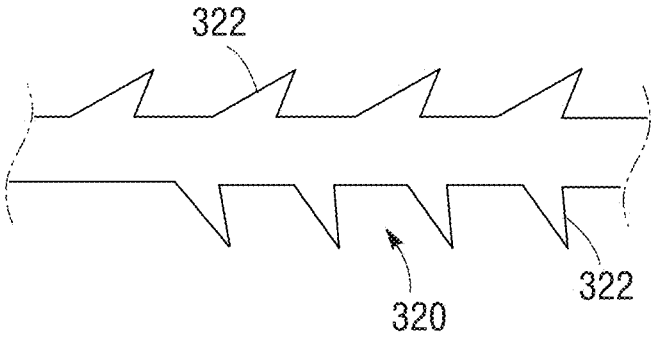
FIG. 12B is a schematic diagram of another embodiment of an actuation member having locking features that can be used with the prosthetic valve delivery assembly of FIG. 1.
Figure 12C:
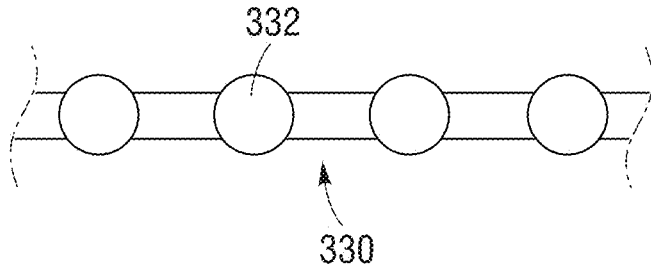
FIG. 12C is a schematic diagram of another embodiment of an actuation member having locking features that can be used with the prosthetic valve delivery assembly of FIG. 1.

In alternative embodiments, the distal end portions of the actuation members 86 can have locking features to promote locking engagement of the jaws 102 of the clamping mechanism 98 with the actuation members 86. FIGS. 12A, 12B, and 12C, for example, show actuation members 310, 320, 330, respectively, that can be used with the locking unit 94 of FIG. 9. With reference to FIG. 12A, the actuation member 310 can include locking features in the form of a plurality of spaced-apart ribs or projections 312 and slots 314 between adjacent ribs. The jaws 102 of the clamp 98 can extend into the slots 314, helping secure the actuation member 86 against movement relative to the clamp 98 in a direction opposite the tension being applied to the actuation member by the user. In other words, the actuation member 86 and the clamp 98 can function as a ratchet that allows the actuation member 86 to be pulled through the clamp 98 in a first direction to expand the frame 22 but the engagement of the jaws 102 in the slots 314 resist movement of the actuation member 86 in a second, opposite direction.

As shown in FIG. 12B, an actuation member 320 can include a plurality of spaced-apart angled barbs 322 that can engage the jaws 102 of the clamp 98. With reference to FIG. 12C, an actuation member 330 can include a plurality of spaced-apart spherical protrusions 332, such as beads, that can engage the jaws 102 of the clamp 98. The barbs 322 and the protrusions 332, like the ribs 312, allow movement of the actuation member through the jaws 102 in a first direction but resist movement in a second, opposite direction.

FIGS. 14A, 14B, 15, and 16A-16D illustrate an alternative release-and-locking unit 410 that can be used with a prosthetic implant delivery assembly, including, for example, the prosthetic implant delivery assembly 10 of FIG. 1. The locking unit 410 can be incorporated in any radially expandable frame of a prosthetic valve or other type of prosthetic implant, including, for example, the frame 22 of FIG. 2 or the frame 200 of FIG. 4.

Figures 14A, 17, 18A, 18B:
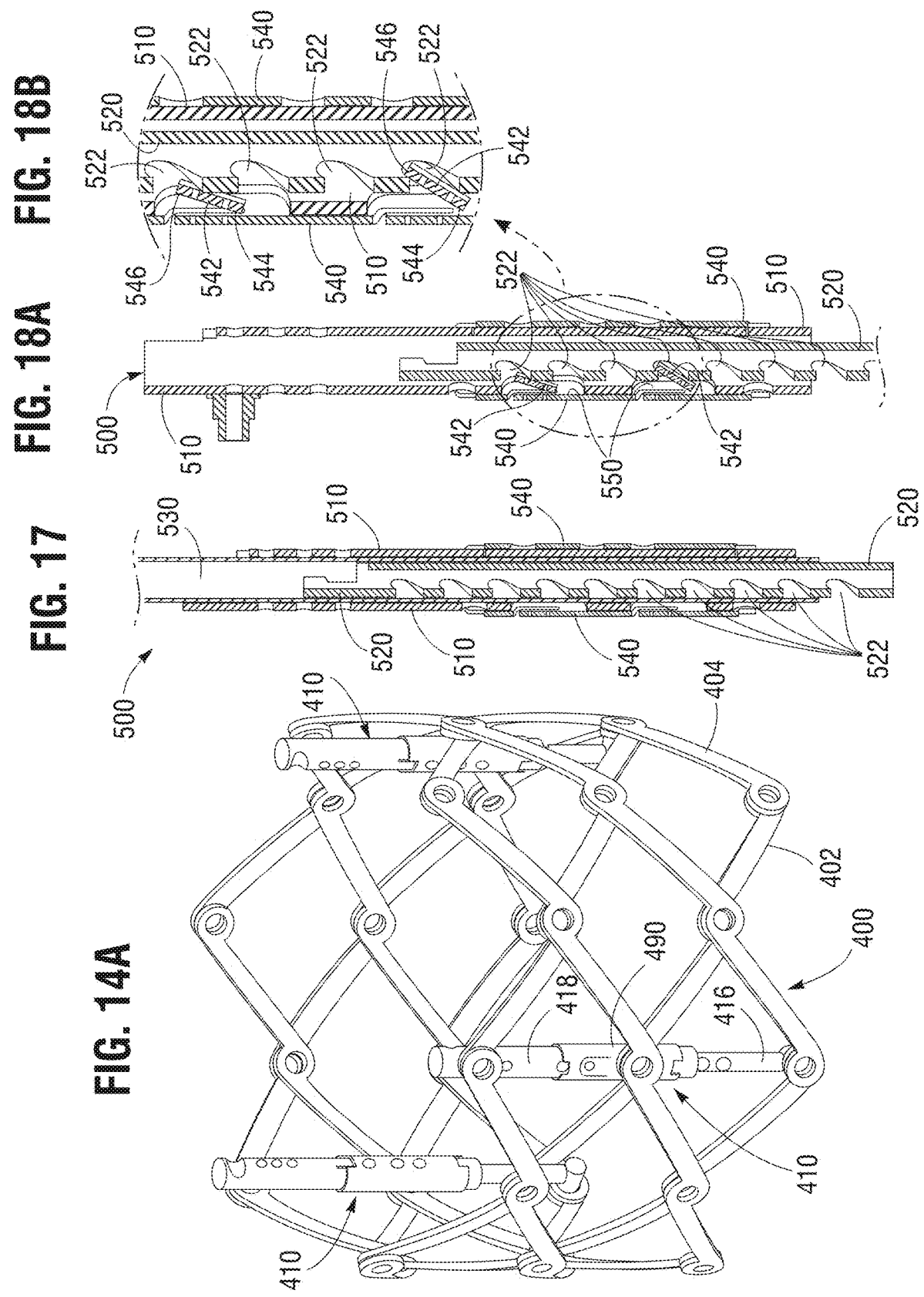
FIG. 14A is a side elevational view of a frame of a prosthetic valve incorporating another embodiment of a locking unit.
FIG. 17 is a cross-section of another embodiment of a locking unit, shown in the unlocked position.
FIG. 18A is a cross-section of the locking unit of FIG. 17, shown in the locked position.
FIG. 18B is an enlarged view of a portion of the locking unit of FIG. 18A.

FIG. 14A shows an exemplary mechanical valve frame 400, which may be used with any of the delivery assemblies of this disclosure. As shown in FIG. 14A, the frame 400 can be constructed of crossing struts 402 and 404 connected to a plurality of locking units 410, which may be used to expand and contract the frame 400, as further described herein. In the illustrated embodiment, there are two layers of struts, namely, inner struts 402 and outer struts 404. In other embodiments (not shown), the struts may be interwoven. One or more locking units 410 (which can also be referred to as "frame expansion devices" or "frame actuators") can be coupled to the frame 400 at circumferentially spaced apart locations (e.g., spaced 120 degrees apart from each other), similar to the locking units 94 described above. In the illustrated embodiment, there are three such locking units 410 coupled to the frame, but it is understood that more or fewer such assemblies could be used.

Figures 14B, 15:
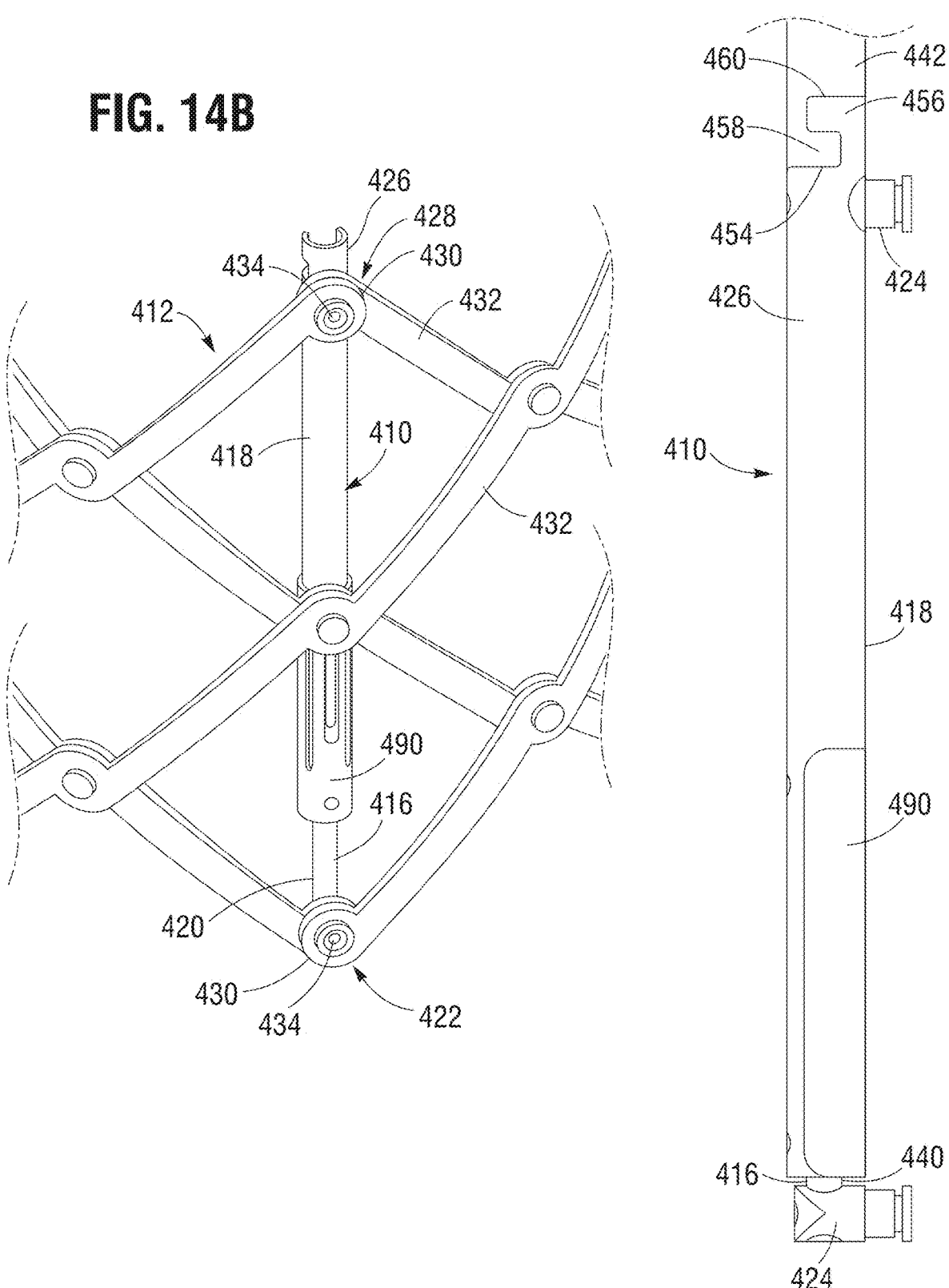
FIG. 14B is a perspective view of a portion of the frame of FIG. 14A.
FIG. 15 is an enlarged side view of the locking unit of FIG. 14A.
Figure 16A:
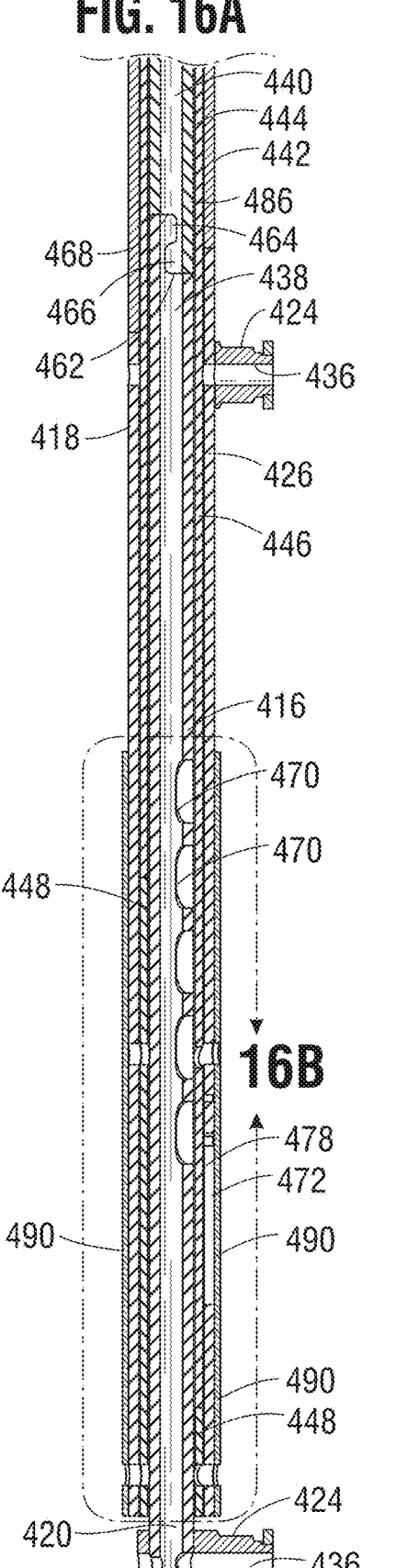
FIG. 16A is a cross-sectional view of the locking unit of FIG. 14A shown in the fully contracted state corresponding to the fully radially expanded state of the prosthetic valve.

With reference to FIG. 14B, the locking unit 410 generally can comprise an inner member 416, such as an inner tubular member, and an outer member 418, such as an outer tubular member, concentrically disposed about the inner member 416. The inner member 416 and the outer member can be moveable longitudinally relative to each other in a telescoping manner to radially expand and contract the frame 400, as further described below. As best shown in FIGS. 14B and 16A, the inner member 416 can have a distal end portion 420 coupled to a distal end 422 of the frame 400 with a coupling element 424. The outer member 418 can have a proximal end portion 426 coupled to a proximal end 428 of the frame 400 with a respective coupling element 424.

The inner member 416 and the outer member 418 can telescope relative to each other between a fully contracted state (as shown in FIG. 15) corresponding to a fully radially expanded state of the prosthetic valve and a fully extended state (wherein the inner member 416 is fully extended from the outer member 418) corresponding to a fully radially compressed state of the prosthetic valve. The locking unit 410 allows the prosthetic valve to be fully expanded or partially expanded to different diameters and retains the prosthetic valve in the partially or fully expanded state.

Each of the coupling elements 424 desirably is connected to a respective apex 430 at the proximal or distal end of the frame. Each apex 430 can be formed by the adjacent end portions of two struts 402, 404 that are pivotally connected to each other with a fastener 434 (e.g., a rivet or pin) that extends through corresponding apertures in the struts. Each coupling element 424 can be pivotally connected to a respective apex 430 by a corresponding fastener 434 that extends into an opening or bore 436 (FIG. 16A) of the coupling element 424. The fastener 434 in the illustrated embodiment therefore connects the end portions of the struts 402, 404 to a coupling element 424 while allowing the struts to pivot relative to each other and the coupling element 424.

In alternative embodiments, the end portions of the struts 402, 404 can be secured to each other and the coupling element without a pinned connection. For example, the frame can be laser cut from a metal tube without pinned connections at each apex and the coupling elements or the end portions of the inner and outer members 416, 418 can be connected to the frame at or adjacent respective apices, such as by welding or sutures.

As further shown in FIG. 16A, a proximal end portion 438 of the inner member 416 can be releasably coupled to an inner actuation member, or shaft, 440 that extends the length of the delivery apparatus to a handle at the proximal end of the delivery apparatus (the handle is not shown but can be similar to the handle 70 of FIG. 1, or any of the other handles described herein). The proximal end portion 426 of the outer member 418 can be releasably coupled to an outer actuation member, or shaft, 442 that extends the length of the delivery apparatus to the handle at the proximal end of the delivery apparatus. The proximal end portions of the inner actuation member 440 and the outer actuation member 442 can be operatively connected to respective actuators or control mechanisms (e.g., rotatable or slidable knobs) in the handle to effect longitudinal movement of the actuation members 440, 442 relative to each other. The inner actuation member 440 can extend coaxially through the outer actuation member 442. The pair of inner and outer actuation members 440, 442 can extend through an outer shaft (not shown, but can be similar to the shaft 72 of FIG. 1) along with other pairs of inner and outer actuation members extending from the other locking units 410. All pairs of inner and outer actuation members 440, 442 can be operatively connected to a common actuator or control mechanism on the handle.

The inner and outer actuation members 440, 442, respectively, are configured to apply proximally and distally directed forces to the inner and outer members 416, 418, respectively, to effect radial expansion and contraction of the frame 400. For example, to expand the frame, the outer actuation member 442 can be moved distally while the inner actuation member 440 is held stationary, thereby causing the outer member 418 to move distally over the inner member 416. As a result, a distally directed force is applied to the proximal end 428 of the frame 400, causing the frame to foreshorten axially and expand radially. Expansion of the frame 400 can also be accomplished by moving the inner actuation member 440 proximally while the outer actuation member 442 is held stationary. Alternatively, the frame 400 can be expanded by moving the inner actuation member 440 proximally and simultaneously moving the outer actuation member 442 distally. The frame 400 can be radially contracted by reversing the direction of movement of the inner and outer actuation members 440, 442.

A release member 444 can extend coaxially between the inner actuation member 440 and the outer actuation ember 442 along the length of the delivery apparatus. A distal end portion 446 of the release member 444 can extend coaxially between the inner member 416 and the outer member 418 of the locking unit 410. The proximal end portion of the release member 444 (not shown) can be operatively connected to a corresponding actuator or control mechanism (e.g., a rotatable or slidable knob) on the handle to effect longitudinal movement of the release member relative to the inner and outer actuation members 440, 442. The locking unit 410 can include a centering tube 448 coaxially disposed between the inner member 416 and the outer member 418 distal to the release member 444. The centering tube 448 helps maintain the outer member 418 in coaxial alignment with respect to the inner member 416 and can be secured, such as by welding, to the outer member 418. The proximal end portions of release members 444 extending from all locking units 410 on the frame can be operatively connected to a common actuator or control mechanism on the handle.

As noted above, the proximal end portion 426 of the outer member 418 can be releasably coupled to the outer actuation member 442. As best shown in FIG. 15, the releasable coupling can be formed by, for example, a notch 454 and a tab 456 formed in the proximal end portion 426 of the outer member 418 and configured to releasably engage a corresponding tab 458 and a notch 460 of the outer actuation member 442. During delivery and expansion of the prosthetic valve, the release member 444 extends through the notches 454, 460 and tabs 456, 458, and can prevent the tab 456 from disengaging from the notch 460, and the tab 458 from disengaging from the notch 454, similar to the tabs 114, 120 and notches 116, 120 of FIG. 10A. When the prosthetic valve is to be released from the delivery apparatus, the release member 444 can be moved proximally of the notches 454, 460 and tabs 456, 458, allowing them to disengage and the outer member 418 and the outer actuation member 442 to disengage and decouple from each other.

The proximal end portion 438 of the inner member 416 can be releasably coupled to the inner actuation member 440 in a similar fashion. For example, the inner member 416 can be coupled to the inner actuation member 440 using a notch 462 and a tab 464 formed in the proximal end portion 438 of the inner member 416 and configured to releasably engage a corresponding tab 466 and a notch 468 of the inner actuation member 440. During implantation and expansion, the release member 444 can extend coaxially over the notches 462, 468 and tabs 464, 466, preventing the inner member 416 and the inner actuation member 440 decoupling. When the prosthetic valve is to be released from the delivery apparatus, the release member 444 can be moved proximally of the notches 462, 468 and tabs 464, 466, allowing them to disengage and the inner member 416 and the inner actuation member 440 to disengage and decouple from each other.

The inner and outer members 416, 418 can include corresponding locking features to retain the frame 400 in an expanded state. In the illustrated embodiment, for example, the inner member 416 can include one or more longitudinally spaced apart apertures or recesses 470 disposed along the length of the inner member 416. The apertures 470 can be configured to receive a locking member 472 of the outer member 418. The locking member 472 can have a fixed end portion 474 secured to the outer member 418, a tapered or reduced-diameter intermediate portion 476, and a free end portion, or latch portion, 478 configured to engage one of the recesses 470.

Figure 16B:
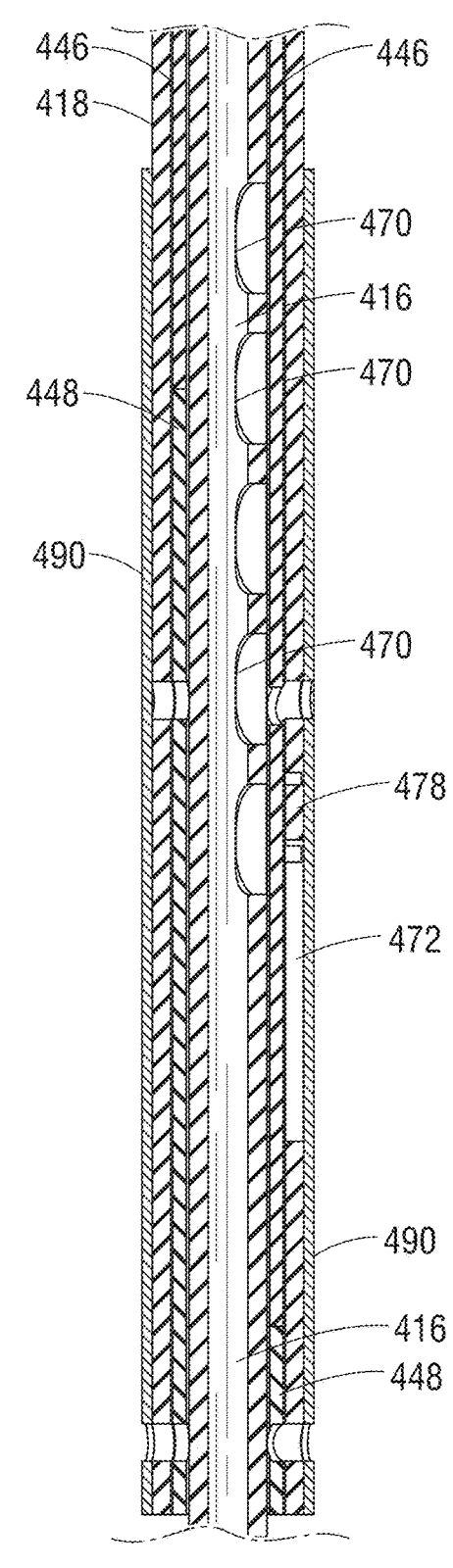
FIG. 16B is an enlarged cross-sectional view of a portion of the locking unit shown in FIG. 16A.

The locking member 472 can be biased radially inwardly toward the inner member 416, such as by shape setting the locking member 472 to bend inwardly toward the inner member. In certain embodiments, for example, the locking member 472 (and, optionally, the entire outer member 422) can be formed from a shape-memory alloy, such as a nickel titanium alloy ("NiTi"), for example Nitinol. When the release member 444 is disposed between the inner member 416 and the outer member 418 during delivery and expansion of the prosthetic valve, the locking member 472 is retained in an unlocked state with the latch portion 478 spaced radially outward of the recesses 470 in the inner member 416 (as best shown in FIG. 16B). When the release member 444 is moved proximally beyond the locking member 472, the locking member 472 can assume its pre-bent shape, indicated by position 480, and the latch portion 478 can extend into a selected recess 470 (as best shown in FIG. 16D). Once the latch portion 478 has entered a recess 470, the inner member 416 and outer member 418 can be secured against relative axial movement thereby resisting radial contraction of the frame from its expanded state.

A rigid sleeve 490 can be mounted over the outer member 418 adjacent the locking member 472 to resist buckling of the locking unit 410 in the area of the locking member 472. The rigid sleeve 490 can be at least generally annular and extend around at least a portion of the outer surface of the outer member 418. In some examples, the rigid sleeve 490 can extend fully about the outer surface of the outer member 418. In other examples, the rigid sleeve 490 can extend for less than the entire outer surface of the outer member 418. In some cases, the rigid sleeve 490 can be fixedly secured to the outer member 418, such as by adhesion or welding.

In use, the prosthetic valve incorporating the frame 400 and locking units 410 can be placed in a compressed state in a sheath of a delivery apparatus, as discussed above in connection with the prosthetic valve 14. A physician can then insert the prosthetic valve into a patient. When the prosthetic valve is at the desired location within the patient, the physician can deploy the prosthetic valve from the sheath and then expand or contract the frame 400 to achieve a desired frame size (diameter) by manipulating the inner and outer actuation members 440, 442, as described above. The prosthetic valve can be deployed from the sheath by retracting the sheath and/or by advancing the inner and outer actuation members in the distal direction to advance from the prosthetic valve from the sheath.

In particular embodiments, the prosthetic valve is fully functional once deployed from the sheath and at least partially expanded. In this manner, the physician can test the operation of the prosthetic valve prior to releasing the prosthetic valve from the delivery apparatus. If needed or desired, the prosthetic valve can be at least partially radially compressed, repositioned (e.g., repositioned superiorly or inferiorly) and then re-expanded. If needed or desired, the prosthetic valve can be fully radially compressed and retrieved back into the sheath of the delivery apparatus and withdrawn from the body.

When the desired size and position of the prosthetic valve has been achieved, the physician can proximally retract the release member 444 until it is located proximal to the locking member 472. The locking member 472 can then assume its pre-curved shape and engage an aperture 470 in the inner member 416 of the locking unit, thereby resisting further relative movement between the inner member 416 and the outer member 418 and retaining the prosthetic valve in its expanded state. As noted above, the handle of the delivery apparatus can include common actuator that controls retraction of all release members 444 extending from corresponding locking units 410 on the frame in embodiments that include plural locking units.

To release the prosthetic valve from the delivery apparatus, the physician can further retract the release member 444 until it is located proximal to the notches 462, 468 and the tabs 464, 466 to de-couple the inner member 416 from the inner actuation member 440 and proximal to the notches 454, 460 and the tabs 458, 456 to de-couple the outer member 418 from the outer actuation member 442. Thereafter, the delivery apparatus can be withdrawn from the body.

It should be appreciated that the locking units 410 and delivery apparatus used therewith may be modified without departing from the scope of the present disclosure. For example, in some implementations, the outer member 418 can be axially moveable relative to a fixed inner member 416, in further implementations the inner member 416 can be axially moveable relative to a fixed outer member 416, and in yet other implementations the inner member 416 and the outer member 418 may both be axially moveable relative to one another. Although the inner member 416 is depicted and described as connected to a distal end 422 of the frame 400, in other implementations the position of the locking unit can be reversed such that the inner member 416 can be connected to the proximal end 428 of the frame 400, and the outer member 418 connected to the distal end 422 of the frame 400.

Similarly, the inner member 416 is described as having apertures 470 and the outer member as having a locking member 472. However, in other implementations, the locking member 472 can be included on the inner member 416 and the apertures 470 can be formed in the outer member 422. Although depicted and described as tubular, the inner member 416, the outer member 418, and the release member 444 can have other shapes or configurations. For example, in one particular implementation, the inner member 416, the outer member 418, and the release member 444 can be formed from flat strips of material, with one of the inner member 416 and the outer member 418 having the apertures 470 and the other having the locking member 472. The flat strips forming the inner member 416, the outer member 418, and the release member 444 can be housed in an elongated housing, such as a shaft or tubular member.

The frames and/or delivery assemblies of the present disclosure can provide a number of advantages. For example, a mechanically expandable frame as described herein can be radially compressed to a delivery configuration and loaded into a delivery apparatus without using a crimping apparatus. Because the frame can be fully expanded or expanded to a desired size less than the fully expanded state, at least in some embodiments, a prosthetic valve as described herein can be implanted in various size annuluses, and the optimal size of the prosthetic valve can be achieved during implantation. In some cases, a delivery assembly of the present disclosure can apply a sufficient expansion force to open or enlarge a calcified native valve, which can reduce or eliminate the need for pre- or post-balloon valvuloplasty.

In addition, as noted above, the prosthetic valve can be fully functional during the implantation procedure, which can reduce or prevent blood flow occlusion and avoid the use of rapid pacing during implantation. The embodiments disclosed herein also can allow for slow deployment of the prosthetic valve, which can allow for tissue stress relaxation, and can reduce the risk of aortic rupture.

FIGS. 17, 18A, and 18B show an alternative locking unit, or locker tube assembly, indicated at 500 (which can also be referred to as a "frame expansion device" or "frame actuator"). A prosthetic heart valve frame (e.g., the frame 400) can include one or more assemblies 500 to control expansion and contraction of the frame and to retain the frame in an expanded, deployed state, similar to the embodiment of FIG. 14A. In the illustrated embodiment, the locker tube assembly 500 comprises an outer member, locker tube, 510 (which may be an extension of, or otherwise connected to an outer actuation member 442 (not shown in FIGS. 17-18B)). The outer locker tube 510 is concentrically disposed about a middle locker tube, or member, 530 (which may be the distal end portion of a release member 444, which is in turn concentrically disposed about an inner locker tube, or member, 520 (which may be an extension of, or otherwise connected to an inner actuation member 440 (not shown in FIGS. 17-18B). Additionally, concentrically disposed about the outer locker tube 510 is a tabs tube 540, which may include one or more locking tabs 542 for locking the outer locker tube 510 to the inner locker tube 520, as further described herein. Alternatively, the locking tabs 542 from the tabs tube 540 may be integrated into the outer locker tube 510.

Additionally, the outer and inner locker tubes 510, 520 can include corresponding locking features to retain a frame, such as frame 400, in an expanded state. In the illustrated embodiment, for example, the inner locker tube 520 can include one or more longitudinally spaced apart apertures or recesses 522 disposed along the length of the inner locker tube 520. The apertures 522 can be configured to receive a locking member (in the illustrated embodiment locking tabs 542) to secure inner locker tube 520 to outer locker tube 510. Each locking tab 542 can have a fixed end portion 544 secured to the tabs tube 540 (or, alternatively, directly to the outer locker tube 510), and a free end portion, or latch portion 546 configured to engage one of the apertures 522.

Each locking tab 542 can be biased radially inwardly toward the inner locker tube 520, such as by shape setting the locking tab 542 to bend inwardly toward the inner locker tube. In certain embodiments, for example, the locking tab 542 (and, optionally, the entire outer locker tube 510) can be formed from a shape-memory alloy, such as a nickel titanium alloy ("NiTi"), for example Nitinol. When the middle locker tube 530 is disposed between the inner locker tube 520 and the outer locker tube 510 during delivery and expansion of the prosthetic valve, the locking tabs 542 are retained in an unlocked state with the latch portions 546 spaced radially outward of the apertures 522 in the inner locker tube 520 (as best shown in FIG. 17). The locking tabs 542 can reside in respective apertures 550 in the outer tube 510 in the unlocked state. When the middle locker tube 530 is moved proximally beyond the tabs tube 540 (or past the portion of the outer locker tube 510 containing locking tabs 542), the locking tabs 542 can assume their pre-bent shape, and the latch portion 546 of each locking tab can extend into a respective aperture 522 (as best shown in FIG. 18B). Once the latch portion 546 of each tab has entered an aperture 522, the inner locker tube 520 and outer locker tube 510 can be secured against relative axial movement thereby resisting radial contraction of the frame from its expanded state.

Additionally, as described above with regard to locking unit 410, a rigid sleeve such as sleeve 490 (not shown in FIGS. 17-18B) can be mounted over the tabs tube 540 or outer locker tube 510 adjacent the locking tabs 542 to resist buckling of the tabs tube 540 and/or the outer locker tube 510 in the area of the locking tabs 542.

The middle locker tube 530 serves as an immobilizer, preventing the locking tabs 542 of the tabs tube 540 from entering the apertures of the inner locker tube 520 until the operator desires to lock the valve assembly, as further described herein. The outer locker tube 510 and inner locker tube 520 can telescope relative to each other to radially expand or compress a mechanical valve frame such as frame 400, e.g., by attaching the outer locker tube 510 to one end of a valve frame (e.g., a proximal end), while attaching the inner locker tube 520 to an opposite end of the valve frame (e.g., a distal end), similar to the attachment of the locking units described in FIGS. 8 and 14B.

Thus, the frame may be expanded (and axially foreshortened) by decreasing the distance of these tubes relative to one other. Conversely, it may be compressed (and lengthened) by increasing the distance of these tubes relative to one another. As one example, the outer locker tube 510 may be affixed at the proximal end of a frame, while the inner locker tube may be affixed at the distal end of the frame. For valve expansion, then, in the cited example, the outer locker tube 510 may be pushed distally while the inner locker tube 520 is pulled in the proximal direction. Alternatively, for valve expansion the outer locker tube 510 may be kept stationary (relative to the handle of the delivery apparatus), while the inner locker tube 520 is pulled in the proximal direction. In still another approach for expanding the valve, the inner locker tube 520 may be held still, while the outer locker tube 510 is pushed distally. It is understood that for valve compression, these relative movements would be reversed. It is further understood that the outer locker tube 510 may alternatively be affixed at a proximal end of the frame, with the inner locker tube 520 affixed at a distal end of the frame, in which case the relative movements of the tubes described would also be reversed.

FIGS. 18A and 18B shows the exemplary locker tube assembly of FIG. 17 in a locked position, e.g., with the middle locker tube 530 removed. As best shown, when middle locker tube 530 is removed, locking tabs 542 on the tab tube 540 are positioned within respective recesses 522 in the inner locker tube 520, preventing movement of the inner locker tube 520 relative to the outer locker tube 510. Thus, the middle locker tube 530 is preferably maintained within the locker tube assembly 500 during expansion and compression of the valve frame, to prevent locking, until the valve frame is properly situated, e.g., at the implantation site.

FIG. 19 illustrates an exemplary actuation sequence for actuating a delivery apparatus and deploying a valve frame (e.g., a frame 400) releasably coupled to the distal end of the delivery apparatus, according to one embodiment of this disclosure. In FIG. 19, the "inner element" can represent an inner tube or element 520 of a locking unit 500 on the frame 500 and/or an inner actuation member 440 coupled to the inner tube 520; the "middle element" can represent a release member 444; and the "outer element" can represent the outer tube or element 510 of the locking unit 500 and/or an outer actuation element 418 coupled to the outer tube 510.

In an Initial state, for example, when a frame is crimped in a compressed state for introduction into a patient, none of an outer element (e.g., outer locker tube 510), an inner element (e.g., inner locker tube 520) and a middle element (e.g., release member 444) are in motion relative to one another.

In a first operable state, State A, which may represent expansion and/or compression of the frame, the middle element moves together with the inner element. In the illustrated embodiment, the outer element is remains stationary. So, in one exemplary embodiment, pushing the release element 444 and the inner locker tube 520 together in the distal direction, while keeping the outer locker tube 510 in place might, for example, result in compressing the valve frame radially, while pulling/retracting the release member 444 and the inner locker tube 520 together proximally, while keeping the outer locker tube 510 in place might result in expanding the valve frame radially.

In a second operable state, State B, which may represent locking the valve frame and releasing the valve from the delivery system, the outer element and the inner element may be kept in place, while the middle element is pulled, e.g, proximally. For example, as illustrated in the embodiment of FIG. 18, upon retraction of the distal end portion 530 of the release member 444 from the space between the locking tabs and the corresponding locking apertures of locking unit 500, the outer locker tube 510 may be fixed (e.g., "locked") relative to the inner locker tube 520. Further retraction of the release member 444 from the locking unit 500 may release the valve frame from the delivery apparatus entirely, or at least partially, in a manner similar to that described with regard to FIGS. 10A and 16A.

FIG. 20 illustrates an exemplary delivery apparatus 600 for delivering and deploying a prosthetic heart valve, such as a prosthetic heart having a frame 400. The delivery apparatus includes, in the illustrated embodiment, a valve actuation handle assembly 602 that is configured to produce movement of first and second elements of the delivery apparatus relative to a third element of the delivery apparatus via an actuation knob and also produce movement of the first element relative to the second and third elements via the same actuation knob. For example, one actuation knob can be used to produce the movement of the components described in State A and to produce the movement of the components described in State B.

In the illustrated embodiment, for example, the handle assembly comprises an actuation knob 604 and a state toggle, or switch, 606. The outer surface 605 of the actuation knob 604 can include a texture, such as ridges, to aid a user in grasping and rotating the actuation knob 604. The outer surface 607 of the state toggle 606 can also include a texture, such as ridges, to aid a user in grasping and rotating the state toggle 606.

The delivery apparatus 600 can also include a steerable catheter 650, which can include a handle 652 and an elongated shaft 654 extending from the handle. The handle 652 can include a steering mechanism, such as a rotatable knob 656 operatively connected to one or more pull wires extending through the shaft 654. Rotation of the knob 656 is effective to change or adjust the curvature of the distal end portion of the shaft 654 to facilitate steering or guiding of the delivery apparatus through the patient's vasculature.

In particular embodiments, a medical device assembly can include the delivery apparatus 600 and a prosthetic heart valve comprising a frame 400 having a plurality of locking units 410 or 500 (three in the illustrated embodiment). For each locking unit 500 (or locking unit 410), the delivery apparatus 600 can have a respective inner actuation member 440 coupled to the inner tube 520, a respective outer actuation member 442 coupled to the outer tube 510, and a respective release member 444. The proximal ends of the inner actuation members 440, the outer actuation members 418, and the release members 444 can be connected to the handle 602 (as further described below). The inner actuation members 440, the outer actuation members 418, and the release members 444 can extend through the shaft 654 of the steerable catheter 650, and the distal end portions of these components can be releasably coupled to respective locking units 500, in the manner previously described.

Figure 21:
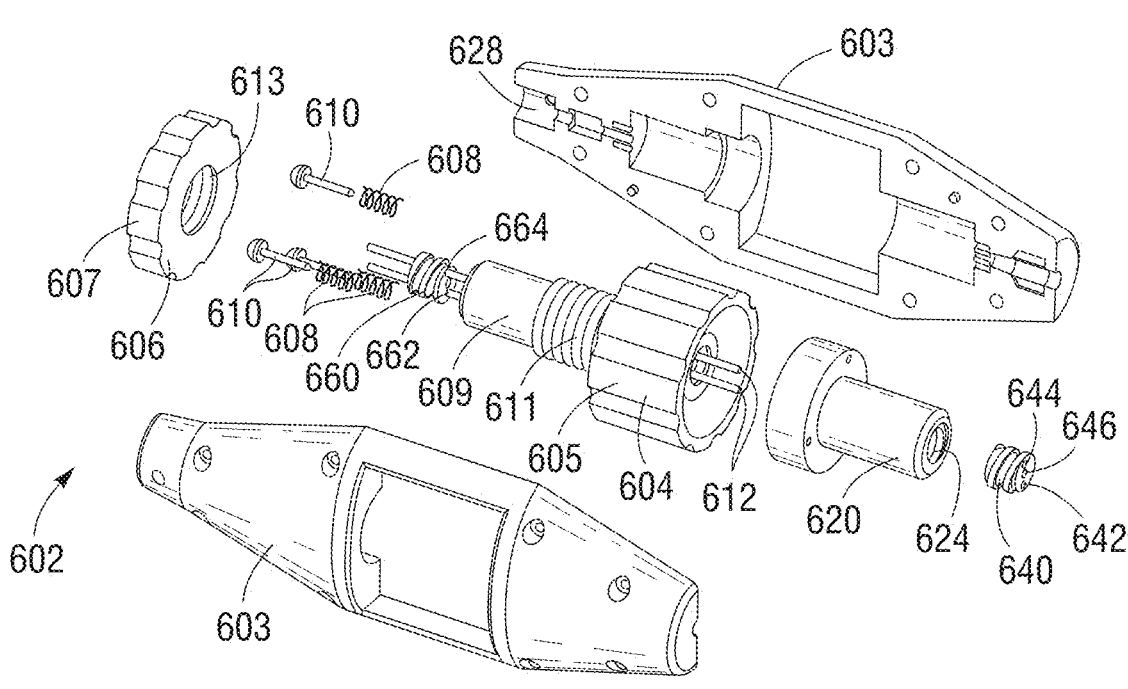
FIG. 21 is an exploded view of the valve actuation handle assembly of FIG. 20.
Figure 22:
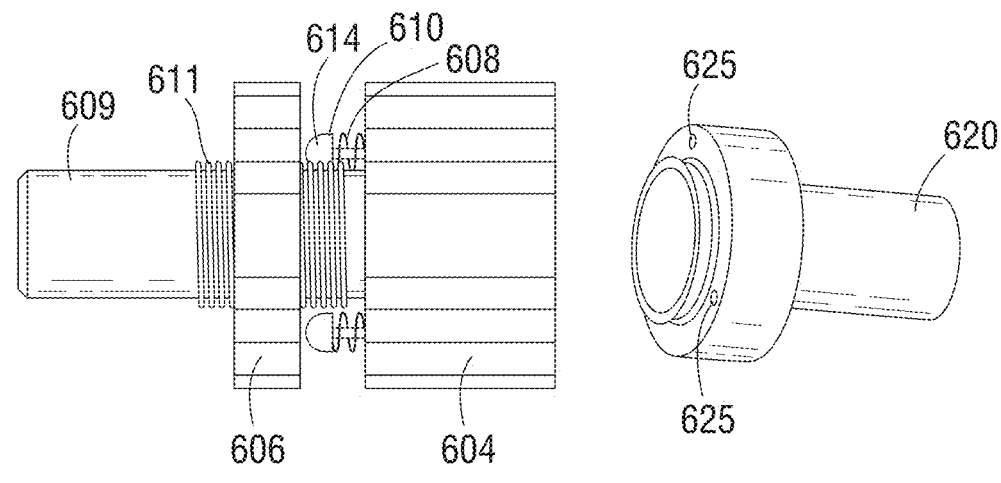
FIG. 22 is a perspective view of the knob mechanism of the valve actuation handle assembly of FIG. 20.

FIG. 21 illustrates an exploded view of the valve actuation handle assembly 602 of FIG. 20. The valve actuation handle assembly 602 can include housing portions 603 housing the actuation knob 604, the toggle 606, a female threaded component 620, an inner tube nut 640 disposed in the female threaded component 620, and a release member nut 660 disposed in an extension portion 609 of the knob 604. The inner tube nut 640 can have external threads that engage internal threads 624 of the female threaded component 620. The extension portion 609 can have internal threads 626 that engage external threads of the release member nut 660 and external threads 611 that engage internal threads 613 of the toggle 606.

Elongated rails 612 can be secured to a component within the handle assembly (e.g., the internal surface of the housing portions 603) and can pass through respective apertures 642, 644 in the inner tube nut 640, and respective apertures 662, 664 in the release member nut 660, preventing the nuts 640, 660 from rotating, resulting in the nuts 640, 660 travelling linearly within the handle assembly upon actuation of the actuation knob 604, as further described below. One or more plungers 610 (three in the illustrated embodiment) can be disposed between the toggle 606 and the distal end portion of the knob 604. Each plunger 610 can extend coaxially through a respective compression spring 608.

Referring also to FIGS. 22 and 26A-26D, state toggle 606 is shown mounted on the external threads 611 of the extension portion 609 of the knob 604. Each plunger 610 has an enlarged head 614 that bears against an adjacent surface of the toggle 606 and a shaft 616 that extends through a corresponding aperture 618 in the knob 604 and into a corresponding bore 625 of the female threaded component 620. Each spring 608 can be retained in a corresponding recess 622 formed within the distal surface of the knob 604 and can bear against the surface of the recess and the enlarged head 614 of the plunger 610. In this manner, each spring 608 biases a corresponding plunger 610 in the distal direction toward the toggle 606.

Figures 26A, 26B, 26C, 26D:
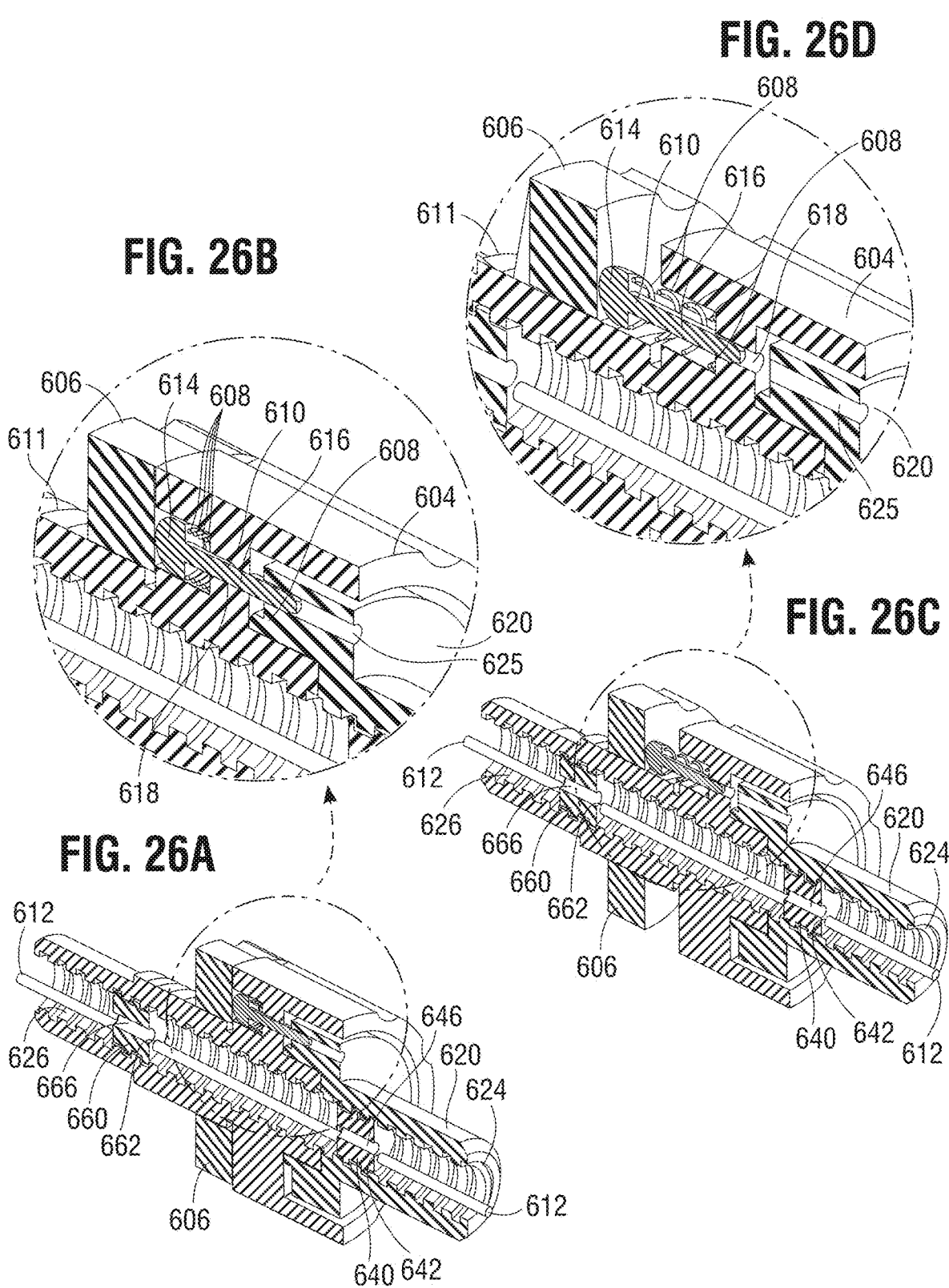
FIG. 26A is a cross-section of the knob mechanism of FIG. 24A toggled into the first state.
FIG. 26B is an enlarged view of a portion of the cross-section of the knob mechanism of FIG. 26A.
FIG. 26C is a cross-section of the knob mechanism of FIG. 24B toggled into the second state.
FIG. 26D is an enlarged view of a portion of the cross-section of the knob mechanism of FIG. 26C.

Rotation of the toggle 606 in a first direction moves the toggle axially along the extension portion 609 in the distal direction toward the knob 604, which causes the shafts 616 of the plungers 610 to move into corresponding bores 625 of the female threaded component 620, as shown in FIGS. 26A-26B. In this position, the plungers 610 couple the knob 604 and the female threaded component 620 such that rotation of the knob 604 causes corresponding rotational movement of the female threaded component 620 in the same direction. This position of the toggle 606 is represented schematically as "State A" in FIG. 19 and is effective to cause radially expansion and compression of the frame 400 upon rotation of the knob 604, as further described below.

Rotation of the toggle 606 in a second direction, opposite the first direction, moves the toggle axially along the extension portion in the distal direction away from the knob 604. As the toggle 606 moves away from the knob 604, the plungers 610 are withdrawn from their corresponding bores 625 under the bias of the springs 608, as shown in FIGS. 26C-26D. In this position, the knob 604 is de-coupled from the female threaded portion 620 such that rotation of the knob 604 does not cause corresponding rotation of the female threaded portion. This position of the toggle 606 is represented schematically as "State B" in FIG. 19 and is effective to lock the frame 400 in an expanded state and de-couple the frame 400 from the delivery apparatus, as further described below.

Figure 23A:
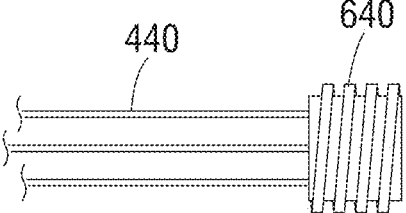
FIG. 23A is a side view showing the connection of inner actuation members to the inner tube nut in the valve actuation handle assembly of FIG. 20.
Figure 23B:
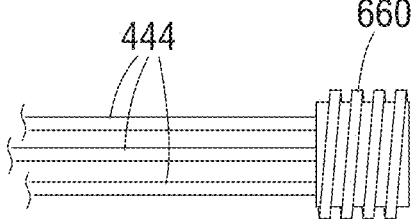
FIG. 23B is a side view showing the connection of release members to the release member nut in the valve actuation handle assembly of FIG. 20.
Figure 23C:
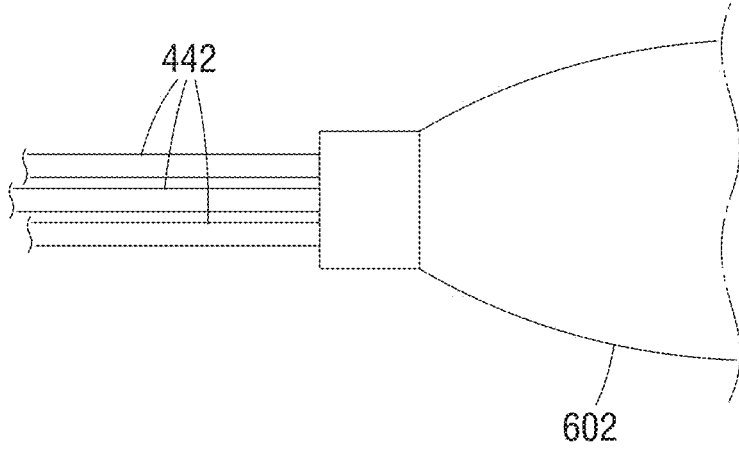
FIG. 23C is a side view showing the connection of outer actuation members to the valve actuation handle assembly of FIG. 20.

As shown in FIGS. 23A-23C, a set of inner actuation members 440 are affixed to the inner tube nut 640. A set of release members 444 is affixed to the release member nut 660 and can pass an aperture 646 in the inner tube nut 640 (the aperture is best shown in FIGS. 26A and 26C). Finally, a set of outer actuation members 442 is affixed to the distal end of the handle 600. For example, the outer actuation members 442 can be fixed inside a bore 628 formed inside the housing portions 603. The members 440, 442, 444 can be affixed to each of the inner tube nut 640, the release member nut 660, and the handle using any of various suitable techniques or mechanisms, such as welding, by adhesion, or by other suitable means. In this manner, axial movement of the inner tube nut 640 causes corresponding axial movement of the inner actuation members 440 in the proximal and distal directions and axial movement of the release member nut 660 causes corresponding axial movement of the release members 440.

While each of the inner tube nut 640, the release member nut 660, and the housing are shown having a set of three members attached thereto, more or less than three such members may be attached to each of these components. In particular embodiments, for example, the number of members 440, 442, 444 in each set corresponding to the number of locking units 500 mounted on the frame of the prosthetic valve. In other embodiments, the inner actuation members 440 can have proximal ends attached to a common shaft, which in turn is affixed to the inner tube nut 640. Similarly, the release members 440 can have proximal ends attached to a common shaft, which in turn is affixed to the release member nut 660.

Rotation of the knob 604 causes corresponding rotation of the extension portion 609, which in turn produces axial movement of the release member nut 660 along the rails 612. Similarly, rotation of the female threaded component 620 produces axial movement of the inner tube nut 640 along the rails 612. As noted above, the knob 604 can either rotate alone, or cause simultaneous rotation of the female threaded component 620, depending on the position of the toggle 606.

Figure 24A:
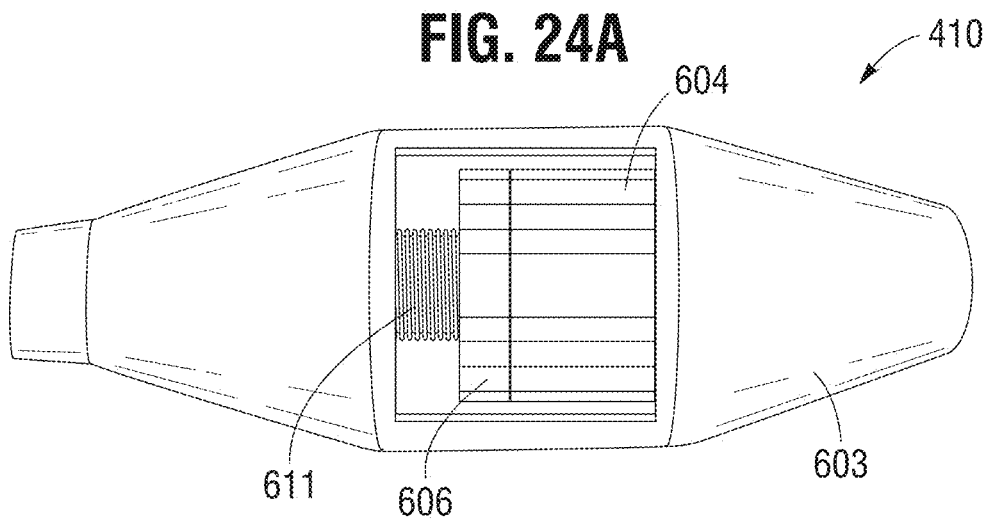
FIG. 24A is a side view of the valve actuation handle assembly of FIG. 20, showing the knob mechanism toggled into a first state.

FIGS. 24A, 26A, and 26B show the toggle in a first position, referred to as "State A" in FIG. 19. In the first position, the toggle 606 retains the plungers 610 within the bores 625 so that rotation of the knob causes corresponding rotation of the female threaded component. Simultaneous rotation of the knob 604 and female threaded portion 620 produces simultaneous axial movement of the nuts 640, 660, and corresponding axial movement of the inner actuation members 440 (and inner tubes 520 on the frame 400) and the release members 444 relative to the outer actuation members 442. Thus, rotation of the knob 604 in a first direction causes the inner actuation members 440 (and inner tubes 520 on the frame 400) and the release members 444 to move proximally relative to the outer actuation members 442 in order to radially expand the frame 400. Conversely, rotation of the knob 604 in a second direction, opposite the first direction, causes the inner actuation members 440 (and inner tubes 520 on the frame 400) and the release members 444 to move distally relative to the outer actuation members 442 in order to radially compress the frame 400.

Figure 24B:
FIG. 24B is a side view of the valve actuation handle assembly of FIG. 20, showing the knob mechanism toggled into a second state.
Figure 25:
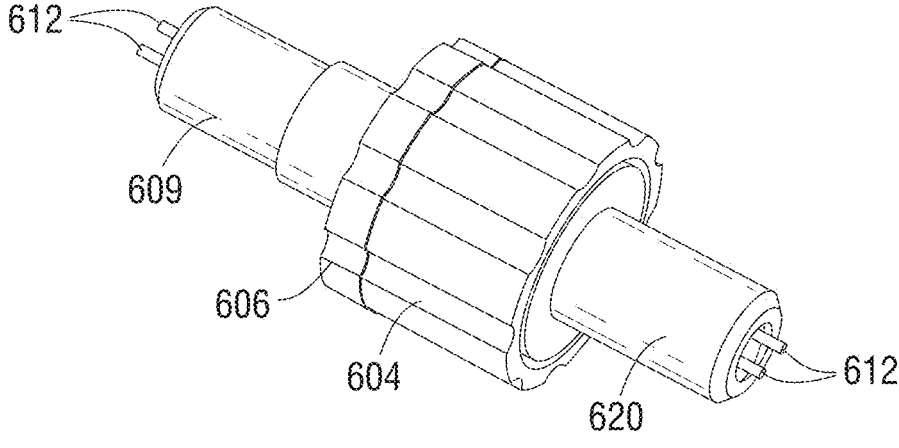
FIG. 25 is a perspective view showing the knob mechanism for the valve actuation handle assembly of FIG. 20.

FIGS. 24B, 26C, and 26D show the toggle in a second position, referred to as "State B" in FIG. 19. In this position, the toggle 606 is moved away from the knob 604 a distance sufficient to allow the plungers 610 to move out of the bores under the bias of the springs 608 such that the knob 604 is de-coupled from the female threaded portion 620. Consequently, rotation of the knob 604 causes corresponding axial movement of the release member nut 660 and corresponding axial movement of the release members 444 relative to the inner actuation members 440 and the outer actuation members 442. Rotation of the knob in a direction that produces movement of the release members 444 in a proximal direction is effective to retract the release members 444 from the locking units 500. As described in detail above, retraction of the release members 444 from the locking units 500 is effective to lock the frame 400 in an expanded state (via locking tabs engaging corresponding apertures) and to release the frame 400 from the delivery apparatus 600.

Switching the toggle 606 from State A to State B may be accomplished, for example, by rotating the toggle a quarter of a rotation (i.e., 90 degrees). In this exemplary embodiment, the toggle 606 and the corresponding threaded portion 611 can have a relatively high pitch. The thread pitch can be, for example, four times the required axial travel of the plungers 610. For example, if the plungers 610 are to axially travel 3 mm for ejection from the corresponding bores 625 of the female threaded component 620, then the toggle thread pitch would be 12 mm, so that a quarter turn of rotation of the toggle 606 will result in the ejection of the plungers 610. In other embodiments, the toggle 606 can have different thread pitches corresponding to different angles of rotation (e.g., 180 degrees, 360 degrees) for moving the toggle between the two states.

Further, the toggle 606 need not be configured for rational movement between the first and second positions. For example, the toggle 606 can be configured to slide axially along the extension portion 609 between the first position and the second position. A mechanical latch or similar mechanism can be used to maintain the toggle 606 in the first position against the bias of the springs 608.

While in the illustrated embodiments, the valve actuation handle assembly 602 is shown as converting rotation of the actuation knob 604 into axial movement of the inner actuation members 440 and release members 444, the disclosed mechanism is not limited to applying axial movement. It can also apply, for example, torque, or rotation, as might be required in other applications. In another embodiment (not shown), by fixing the inner actuation members 440 to the female threaded component 620 and fixing the release members to the actuation knob 604 (and, in one such embodiment, omitting the inner tube nut 640, middle tube nut 660, and the rails 612), turning the actuation knob 604 can apply rotation or torque to the inner actuation member 440 and release member 444. Therefore, this mechanism can also enable rotation of selected components of the delivery apparatus and/or a prosthetic valve relative to other components in a given sequence with the use of a single knob, as well.

Figures 27A, 27B:
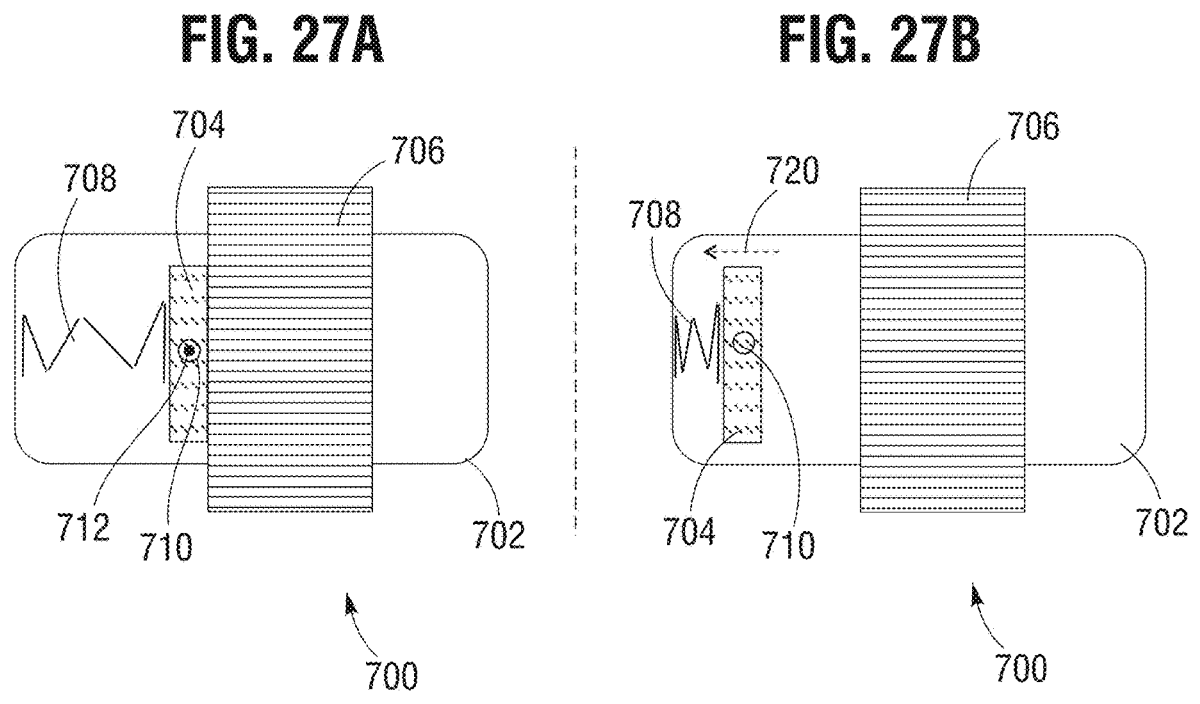

Similarly, FIGS. 27A-27B show an embodiment having a slidable toggle. In particular, FIGS. 27A-27B show a valve actuation handle assembly 700, according to another embodiment, which comprises a housing 702, a toggle in the form of a trigger or toggle plate 704 disposed in the housing, a rotatable knob 706, and a tension spring 708. The spring 708 has one end connected to the trigger plate 704 and another end secured to an inner surface of the housing 702. The trigger plate 704 can have an aperture 710 that is configured to receive a removable pin 712.

FIG. 27A shows the trigger plate 704 in a first position (e.g., corresponding to "State A" in FIG. 19). In this position, the pin 712 extends through the aperture 710 and into a corresponding aperture in the housing 702, which maintains the trigger plate 704 in a position adjacent the knob 706. Further, in this position, the trigger plate 704 can be configured to retain plungers (e.g., plungers 610) in a corresponding openings of a rotatable component (e.g., female threaded component 620) such that rotation of the knob 706 causes corresponding rotation of the rotatable component and corresponding axial movement of two elements relative to another element of the delivery apparatus (e.g., inner actuation members 440 and the release members 444 move relative to the outer actuation members 442).

FIG. 27B shows the trigger plate in a second position (e.g., correspond to "State B" in FIG. 19). To achieve this position, the pin 712 is removed from the aperture 710, which allows the tension spring 708 to move the trigger plate 704 away from the knob 706 as indicated by arrow 720. Movement of the trigger plate 704 to the second position withdraws the plungers from the rotatable component (e.g., female threaded component 620) to de-couple the knob 706 from the rotatable component. As such, rotation of the knob 706 only produces axial movement of one element relative to the other elements of the delivery apparatus (e.g., release members 444 move relative to the inner actuation members 440 and the outer actuation members 442).

While in the embodiments described herein, the two-state actuation system is illustrated as actuating tubes for a collapsible/expandable frame for a heart valve, the embodiments described herein can be advantageously employed in other implementations for delivering and deploying other types of medical devices, such as stents and stent-grafts.

GENERAL CONSIDERATIONS

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device away from the implantation site and toward the user (e.g., out of the patient's body), while distal motion of the device is motion of the device away from the user and toward the implantation site (e.g., into the patient's body). The terms "longitudinal" and "axial" refer to an axis extending in the proximal and distal directions, unless otherwise expressly defined.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method comprising:
    rotating an actuation knob of a medical device assembly to move first and second elements of the medical device assembly relative to a third element of the medical device assembly, wherein such rotating occurs in a first operation state of the medical device assembly;
    actuating a toggle to toggle the actuation knob from the first operation state to a second operation state;
    after actuating the toggle, further rotating the actuation knob to move the first element relative to the second and third elements; and
    in the first operation state, rotating the actuation knob in a first direction to radially expand a prosthetic medical device from a radially collapsed state to a radially expanded state.

2. The method according to claim 1, wherein actuating the toggle comprises moving the toggle relative to the actuation knob from a first toggle position to a second toggle position to toggle the actuation knob from the first operation state to the second operation state.

3. The method according to claim 1, wherein the toggle comprises a knob, and further wherein actuating the toggle comprises rotating the knob in a first direction to move the toggle from a first toggle position to a second toggle position.

4. The method according to claim 1, further comprising, in the first operation state, rotating the actuation knob in a second direction to radially collapse the prosthetic medical device.

5. The method according to claim 1, further comprising, in the second operation state, rotating the actuation knob to lock the prosthetic medical device in the radially expanded state.

6. The method according to claim 5, further comprising, in the second operation state, further rotating the actuation knob to at least partially release the prosthetic medical device from a delivery apparatus of the medical device assembly.

7. The method according to claim 1, wherein the prosthetic medical device is operatively coupled to the actuation knob by the first, second, and third elements and wherein the method further comprises:

rotating the actuation knob in the first operation state to move the first and second elements axially relative to the third element to radially expand the prosthetic medical device.

8. A method for delivering a medical device comprising a prosthetic heart valve in a patient's body utilizing a delivery assembly comprising a handle having a longitudinal axis, at least a first element, a second element, and a third element extending from the handle, an actuation knob configured to actuate at least one of the elements, and a toggle configured to toggle the actuation knob between a first state and a second state, the method comprising:

with the actuation knob in a first state, rotating the actuation knob to move the first and second elements axially relative to the third element;

with the actuation knob in a second state, rotating the actuation knob to move the first element axially relative to the second and third elements;

moving the toggle axially along the longitudinal axis relative to the actuation knob between a first toggle position and a second toggle position to toggle the actuation knob:

from the first state to the second state, and/or from the second state to the first state;

wherein the prosthetic heart valve comprises a radially expandable and compressible frame that is expandable from a radially compressed, delivery state to a radially expanded state, and the first, second, and third elements have respective distal end portions releasably coupled to the frame, the method further comprising:

rotating the actuation knob in the first state to radially expand the frame from the delivery state to the expanded state; and rotating the actuation knob in the second state to release the frame from the distal end portions of the first, second, and third elements.

9. The method of claim 8, wherein the toggle comprises a toggle knob, and further wherein the method comprises rotating the toggle knob in a first direction to move from the first toggle position to the second toggle position.

10. The method of claim 8, wherein the delivery assembly further comprises one or more plungers disposed between the toggle and the actuation knob, the method further comprising moving the plungers between a first plunger position and a second plunger position upon movement of the toggle toward and away from the actuation knob, wherein:

when the plungers are in the first plunger position, the plungers extend through the actuation knob and into a rotatable component such that rotation of the actuation knob causes rotation of the rotatable component and when the plungers are in the second plunger position, the plungers are withdrawn from the rotatable component such that rotation of the actuation knob does not cause corresponding rotation of the rotatable component.

11. A method for delivering a medical device comprising a prosthetic heart valve using a delivery apparatus for implanting a medical device in a patient's body, the delivery apparatus comprising:

a handle;

at least a first element, a second element, and a third element extending from the handle;

an actuation knob configured to actuate at least one of the elements;

a toggle configured to toggle the actuation knob between a first state and a second state;

a rotatable component disposed in the handle; and one or more plungers disposed between the toggle and the actuation knob, wherein the actuation knob is operatively coupled to the first element and the rotatable component is operatively coupled to the second element, but not the first element, the method comprising:

with the actuation knob in the first state, rotating the actuation knob to move the first and second elements axially relative to the third element, wherein rotation of the actuation knob causes corresponding rotation of the rotatable component, the rotation of the actuation knob causing axial movement of the first element and the rotation of the rotatable component causing axial movement of the second element;

with the actuation knob in the second state, rotating the actuation knob to move the first element axially relative to the second and third elements; and actuating the toggle to move the plungers between a first plunger position and a second plunger position upon movement of the toggle toward and away from the actuation knob, wherein:

when the plungers are in the first plunger position, the plungers extend through the actuation knob and into the rotatable component such that rotation of the actuation knob causes rotation of the rotatable component, and when the plungers are in the second plunger position, the plungers are withdrawn from the rotatable component such that rotation of the actuation knob does not cause corresponding rotation of the rotatable component.

12. The method of claim 11, further comprising with the actuation knob in the second state, rotating the actuation knob to cause axial movement of the first element without corresponding rotation of the rotatable component and axial movement of the second element.

13. The method of claim 11, wherein the delivery apparatus further comprises one or more springs configured to bias the one or more plungers to the second plunger position, and wherein actuating the toggle comprises overcoming the spring force of the one or more springs to move the toggle toward the actuation knob so that the plungers extend through the actuation knob and into the rotatable component.

14. The method of claim 11, further comprising extending each of the plungers through an aperture in the actuation knob and into a corresponding opening in the rotatable component when the plungers are in the first plunger position, and withdrawing each of the plungers from the corresponding opening in the rotatable component when the plungers are in the second plunger position.

15. The method of claim 11, wherein the delivery apparatus further comprises a first nut threadably engaging a corresponding threaded portion of the actuation knob and coupled to a proximal end portion of the first element, and a second nut threadably engaging a corresponding threaded portion of the rotatable component and coupled to a proximal end portion of the second element, the method further comprising:

rotating the actuation knob to cause corresponding axial movement of the first nut and the first element, and rotating the rotatable component to cause corresponding axial movement of the second nut and the second element.

16. The method of claim 11, wherein the prosthetic heart valve comprises a radially expandable and compressible frame that is expandable from a radially compressed, delivery state to a radially expanded state, and the first, second, and third elements have respective distal end portions releasably coupled to the frame, the method further comprising:

rotating the actuation knob in the first state to radially expand the frame from the delivery state to the expanded state, and rotating the actuation knob in the second state to release the frame from the distal end portions of the first, second, and third elements.

17. The method of claim 11, wherein:

the prosthetic heart valve comprises a radially expandable and compressible frame comprising at least one expansion and locking unit comprising first and second members, the first member being configured to apply a proximally directed force to the frame and the second member being configured to apply a distally directed force to the frame such that relative axial movement between first and second members is effective to radially expand and/or compress the frame;

the first and second members comprise respective, matable locking features configured to retain the frame in an expanded state when a locking feature of the first member engages a locking feature of the second member;

a distal end portion of the first element extends between the first and second members and prevents the locking feature of the first member from engaging the locking feature of the second member;

a distal end portion of the second element is releasably connected to the first member; and a distal end portion of the third element is releasably connected to the second member, the method further comprising:

rotating the actuation knob in the first state to move the first member relative to the second member to radially expand the frame to the expanded state; and rotating the actuation knob in the second state to retract the distal end portion of the first element from between the first and second members to allow engagement of the locking features of the first and second members.

18. The method of claim 17, further comprising rotating the actuation knob in the second state to at least partially release the prosthetic heart valve from the delivery apparatus.

* * * * *